(12) United States Patent
Kato et al.

(10) Patent No.: US 11,932,836 B2
(45) Date of Patent: Mar. 19, 2024

(54) ELECTRIC REACTION MEASURING APPARATUS, ELECTRIC REACTION PROCESSING METHOD, AND RECORDING MEDIUM

(71) Applicant: Panasonic Intellectual Property Management Co., Ltd., Osaka (JP)

(72) Inventors: Yumiko Kato, Osaka (JP); Kiyotaka Tsuji, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 930 days.

(21) Appl. No.: 16/920,356

(22) Filed: Jul. 2, 2020

(65) Prior Publication Data

US 2020/0333285 A1 Oct. 22, 2020

Related U.S. Application Data

(63) Continuation of application No. PCT/JP2019/006439, filed on Feb. 21, 2019.

(30) Foreign Application Priority Data

Mar. 13, 2018 (JP) ................................. 2018-046060

(51) Int. Cl.
*C12M 1/34* (2006.01)
*C12M 1/32* (2006.01)

(52) U.S. Cl.
CPC .......... *C12M 1/3407* (2013.01); *C12M 23/12* (2013.01); *C12M 41/46* (2013.01)

(58) Field of Classification Search
CPC ..... C12M 1/3407; C12M 23/12; C12M 41/46
See application file for complete search history.

(56) References Cited

U.S. PATENT DOCUMENTS

2002/0113607 A1 8/2002 Yukimasa

FOREIGN PATENT DOCUMENTS

| JP | 2002-031617 | 1/2002 |
| JP | 2011-509697 | 3/2011 |
| JP | 2014-512925 | 5/2014 |
| WO | 2009/073672 | 6/2009 |
| WO | 2012/151498 | 11/2012 |

OTHER PUBLICATIONS

International Search Report of PCT application No. PCT/JP2019/006439 dated Mar. 19, 2019.
Thomas Pfeiffer et al., "Rapid functional evaluation of beta-cells by extracellular recording of membrane potential oscillations with microelectrode arrays", Pflugers Arch—European Journal of Physiology, vol. 462, Sep. 24, 2011, pp. 835-840.

*Primary Examiner* — Jerry Lin
(74) *Attorney, Agent, or Firm* — WENDEROTH, LIND & PONACK, L.L.P.

(57) ABSTRACT

An electric reaction measuring apparatus measures a potential of each of measurement electrodes, which are respectively disposed in chambers in a culture vessel, with respect to at least one reference electrode. The electric reaction measuring apparatus includes at least one control circuit. A measurement object is disposed in each of the chambers. The at least one control circuit calculates at least one principal component for each of the measurement electrodes by performing principal component analysis of the potential of each of the measurement electrodes; estimates, for each of the measurement electrodes, a potential corresponding to the principal component from the principal component of the measurement electrode, and synthesizes the estimated potential; subtracts the synthesized potential of the measurement electrode from a potential measured at the measurement electrode; and outputs a potential after subtraction.

9 Claims, 22 Drawing Sheets

FIG. 6

| TIME | MEASUREMENT ELECTRODE 120b1 | MEASUREMENT ELECTRODE 120b2 | ..... | MEASUREMENT ELECTRODE 120bm |
|---|---|---|---|---|
| t | Vb1 | Vb2 | | Vbm |
| t+a | Vb1a | Vb2a | | Vbma |
| t+2a | Vb1b | Vb2b | | Vbmb |
| ⋮ | ⋮ | ⋮ | ⋮ | |

FIG. 15A

| | ELECTRODE 120bk+1 | | | | |
|---|---|---|---|---|---|
| ELECTRODE 120bk | FIRST PRINCIPAL COMPONENT | SECOND PRINCIPAL COMPONENT | THIRD PRINCIPAL COMPONENT | FOURTH PRINCIPAL COMPONENT | FIFTH PRINCIPAL COMPONENT |
| FIRST PRINCIPAL COMPONENT | | 0.13 | | | |
| SECOND PRINCIPAL COMPONENT | 0.13 | | 0.7 | -0.4 | -0.1 |
| THIRD PRINCIPAL COMPONENT | 0.8 | -0.6 | -0.7 | -0.3 | 0.1 |
| FOURTH PRINCIPAL COMPONENT | -0.5 | -0.1 | -0.8 | -0.7 | 0.5 |
| FIFTH PRINCIPAL COMPONENT | 0.1 | 0.2 | 0.6 | -0.4 | -0.3 |

FIG. 15B

| | ELECTRODE 120bk+3 | | | | |
|---|---|---|---|---|---|
| | FIRST PRINCIPAL COMPONENT | SECOND PRINCIPAL COMPONENT | THIRD PRINCIPAL COMPONENT | FOURTH PRINCIPAL COMPONENT | FIFTH PRINCIPAL COMPONENT |
| ELECTRODE 120bk+2 — FIRST PRINCIPAL COMPONENT | | 0.5 | 0.9 | -0.1 | -0.6 |
| SECOND PRINCIPAL COMPONENT | 0.6 | | 0.1 | 0.5 | 0.2 |
| THIRD PRINCIPAL COMPONENT | 0.8 | -0.2 | | 0.7 | -0.2 |
| FOURTH PRINCIPAL COMPONENT | -0.3 | 0.6 | 0.6 | | 0.1 |
| FIFTH PRINCIPAL COMPONENT | -0.5 | -0.1 | -0.5 | 0.3 | |

FIG. 18

|  | FIRST PRINCIPAL COMPONENT | SECOND PRINCIPAL COMPONENT | THIRD PRINCIPAL COMPONENT | FOURTH PRINCIPAL COMPONENT | FIFTH PRINCIPAL COMPONENT |
|---|---|---|---|---|---|
| FIRST PRINCIPAL COMPONENT | | | | | |
| SECOND PRINCIPAL COMPONENT | 0.13 | | | | |
| THIRD PRINCIPAL COMPONENT | 0.78 | 0.21 | | | |
| FOURTH PRINCIPAL COMPONENT | 0.57 | 0.02 | 0.72 | | |
| FIFTH PRINCIPAL COMPONENT | 0.12 | 0.06 | 0.33 | 0.27 | |

ELECTRIC REACTION MEASURING APPARATUS, ELECTRIC REACTION PROCESSING METHOD, AND RECORDING MEDIUM

BACKGROUND

1. Technical Field

The present disclosure relates to an electric reaction measuring apparatus, an electric reaction processing method, and a recording medium.

2. Description of the Related Art

Cultured cells and tissues are used in various medical and industrial fields to produce cells and tissues for treatment, to test the efficacy of drugs, and for other purposes. In such fields, there is a demand for non-invasive evaluation of the activity of a cultured cell or tissue. However, by microscopic observation, which has been conventionally used, it is difficult to observe a cell activity other than an activity that changes the shape of a cell or a tissue. For example, Patent Document 1 (Japanese Patent No. 3909738) and Non-Patent Document 1 (Thomas Pfeiffer et. al., "Rapid functional evaluation of beta-cells by extracellular recording membrane potential oscillations with microelectrode arrays", Pfluegers Archiv European Journal of Physiology, December 2011, Vol. 462, Issue 6, pp. 835-840) describe a method for evaluating the activity of cultured cells or tissues by exposing measurement electrodes at a surface of a bottom portion of a culture dish and by measuring an electrical reaction that occurs in accordance with the activity of cells that are in contact with the electrodes. Patent Document 2 (Japanese Patent No. 6072005) describes a method in which principal component analysis is used to extract an activity in a living body when measuring an electric reaction of the living body by using electrodes.

SUMMARY

In cell culture and tissue culture for treatment, it is necessary to select cells and tissues that can be used for treatment. Moreover, it is usually difficult to observe an electric reaction of a living body, such as a cell or tissue, because the electric reaction is very weak. With the method described in Patent Document 1 and Non-Patent Document 1, electric reactions of multiple cells or tissues are reflected on the measurement electrodes. With the method described in Patent Document 2, when a noise and a signal common to the electrodes are recorded, it may be difficult to determine which of the cells or tissues has caused a component of the recorded electrical reaction.

One non-limiting and exemplary embodiment of the present disclosure provides an electric reaction measuring apparatus, an electric reaction processing method, and a recording medium each of which reduces noise common to measurement electrodes.

In one general aspect, the techniques disclosed here feature an electric reaction measuring apparatus measures a potential of each of measurement electrodes, which are respectively disposed in chambers in a culture vessel, with respect to at least one reference electrode. The electric reaction measuring apparatus includes at least one control circuit. A measurement object is disposed in each of the chambers. The at least one control circuit calculates at least one principal component for each of the measurement electrodes by performing principal component analysis of the potential of each of the measurement electrodes; estimates, for each of the measurement electrodes, a potential corresponding to the principal component from the principal component of the measurement electrode, and synthesizes the estimated potential; subtracts the synthesized potential of the measurement electrode from a potential measured at the measurement electrode; and outputs a potential after subtraction.

It should be noted that general or specific embodiments may be implemented in a system, a method, an integrated circuit, a computer program, a storage medium, or any selective combination thereof.

With the electric reaction measuring apparatus, the electric reaction measuring method, and the recording medium according to the present disclosure, it is possible to reduce noise common to measurement electrodes.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6 illustrates an example of contents stored in a memory of a processing unit in FIG. 1;

FIG. 15A illustrates an example of some of calculation results obtained by a correlation function processor of the electric reaction measuring apparatus according to the second embodiment;

FIG. 15B illustrates an example of some of calculation results obtained by the correlation function processor of the electric reaction measuring apparatus according to the second embodiment;

FIG. 18 illustrates an example of some of calculation results obtained by a grouping processor of the electric reaction measuring apparatus according to the second embodiment.

DETAILED DESCRIPTION

Figure 1:
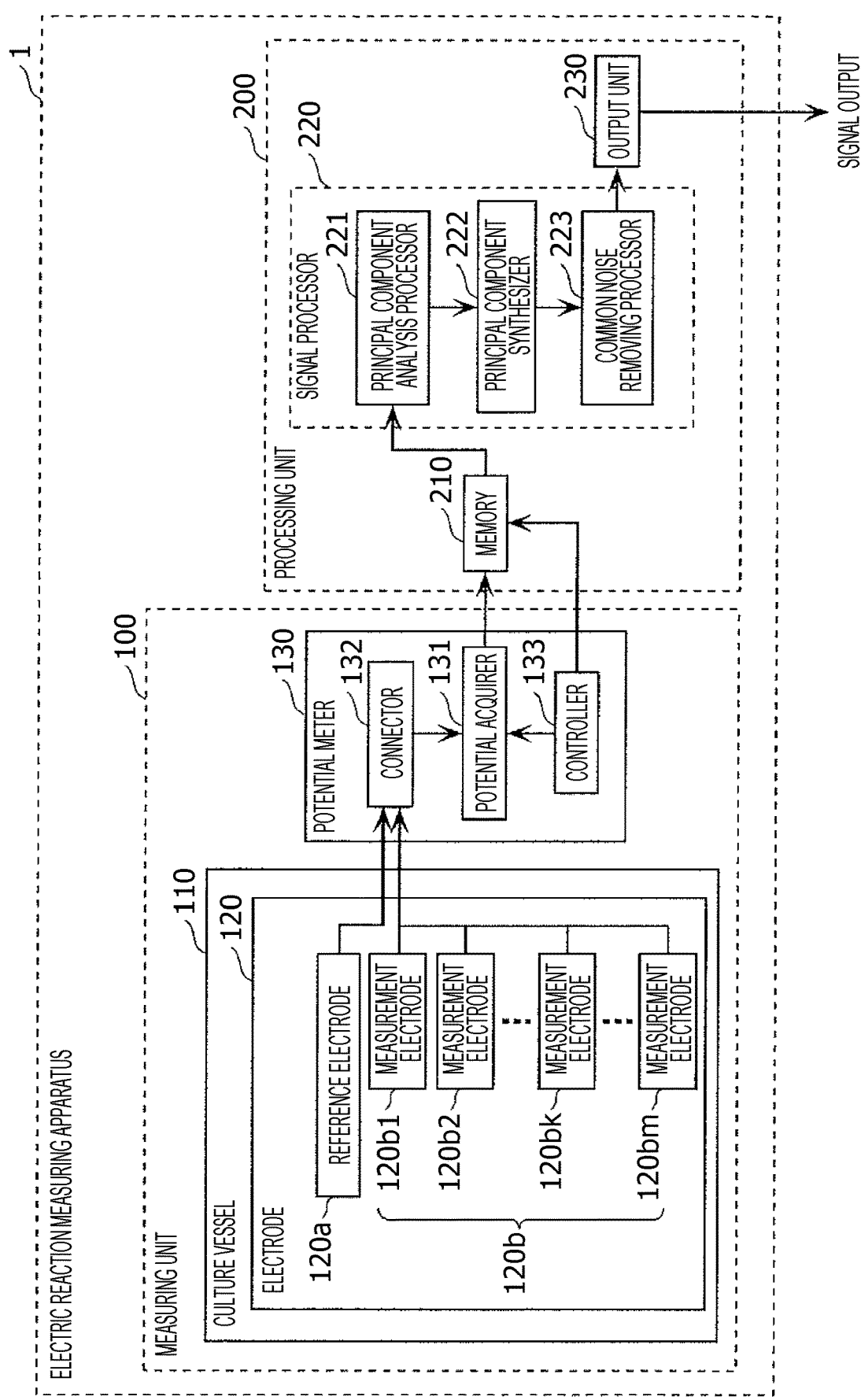
FIG. 1 is a block diagram illustrating an example of the functional configuration of an electric reaction measuring apparatus according to a first embodiment.

The inventors related to the present disclosure have found the following. The inventors examined technologies for non-invasively evaluating the activity of a cultured cell or a cultured tissue. The inventors focused on and examined technologies that use an electrical reaction of a cell or the like to evaluate various activities of the cell or the like. However, with existing technologies, such as those described in Patent Documents 1 and 2 and Non-Patent Document 1, electric reactions of multiple cells or tissues may be reflected on a measurement result of measuring an electric reaction obtained by using a measurement electrode that is in contact with a cell or tissue. Moreover, when measurement is performed by using multiple measurement electrodes, a measurement result of measuring an electric reaction at each measurement electrode may include a common noise and a common signal. Thus, the measurement result obtained at each measurement electrode cannot accurately represent an electric reaction of a cell or the like that is in contact with the measurement electrode.

Therefore, the inventors examined technology for reducing noise common to measurement electrodes. To be specific, the inventors examined technology that reduces noise by using the shape of a culture vessel for culturing cells or tissues, the disposition of electrodes, and a statistical method. The inventors have found that noise can be reduced by disposing a measurement electrode in each of chambers, such as wells, of a culture vessel; measuring time-series data of potentials measured for a cultured cell or tissue in each chamber at each measurement electrode; extracting a component common to the measurement electrodes by using principal component analysis; and obtaining the remainder of a principal component for each measurement electrode. Thus, the inventors have devised the following technology.

An electric reaction measuring apparatus according to an aspect of the present disclosure measures a potential of each of measurement electrodes, which are respectively disposed in chambers in a culture vessel, with respect to at least one reference electrode. The electric reaction measuring apparatus includes at least one control circuit. A measurement object is disposed in each of the chambers. The at least one control circuit calculates at least one principal component for each of the measurement electrodes by performing principal component analysis of the potential of each of the measurement electrodes; estimates, for each of the measurement electrodes, a potential corresponding to the principal component from the principal component of the measurement electrode, and synthesizes the estimated potential; subtracts the synthesized potential of the measurement electrode from a potential measured at the measurement electrode; and outputs a potential after subtraction.

With the above aspect, a potential obtained by synthesizing the potential corresponding to a principal component estimated from a principal component coefficient and a principal component score of a measurement electrode is capable of representing noise at the measurement electrode. Moreover, the noise, which is estimated from the principal component coefficient and the principal component score, takes into consideration the features characteristic to the measurement electrode, such as the position relative to the reference electrode, and is a noise common to the measurement electrodes. A potential that is obtained by subtracting the noise from a potential measured at a measurement electrode is a potential from which a noise common to the measurement electrodes is effectively reduced. Thus, the electric reaction measuring apparatus can reduce, at each measurement electrode, noise common to the measurement electrodes and can extract a component that is recorded specifically at each measurement electrode. Further, the electric reaction measuring apparatus can extract and reduce noise that has been mixed into the measurement electrodes from one noise source, and can accurately extract an electric reaction derived from a measurement object that differs between measurement electrodes.

An electric reaction measuring apparatus according to an aspect of the present disclosure may further include the measurement electrodes and the at least one reference electrode.

An electric reaction measuring apparatus according to an aspect of the present disclosure may further include a partition wall that electrically separates the chambers from each other.

With the above aspect, the partition wall can suppress influence of the potential of a measurement electrode on the potential of another measurement electrode. Thus, the detection accuracy of the potential at each measurement electrode is improved, and electric reaction measuring apparatus can output a processing result with high accuracy.

In the electric reaction measuring apparatus according to an aspect of the present disclosure, the measurement electrodes are disposed inside of the partition wall surrounding the chambers, and the reference electrode is disposed on the partition wall.

With the above aspect, it is possible to suppress variation in the distances between the measurement electrodes and the reference electrode. Thus, in the potential at each measurement electrode, an influence due to the distance from the reference electrode, that is, variation can be reduced.

In the electric reaction measuring apparatus according to an aspect of the present disclosure, the at least one control circuit calculates, for each of the at least one principal component, a contribution ratio of the principal component to a variance of all measured potentials; extracts, from the at least one principal component, some of the at least one principal component in descending order of the contribution ratio; and synthesizes, for each of the extracted principal components, potentials corresponding to the extracted principal components.

With the above aspect, as the contribution ratio of a principal component increases, that principal component can more adequately account for potential variation due to noise common to the entire data. A synthesized potential synthesized from potentials corresponding to principal components extracted in descending order of contribution ratio can effectively represent noise feature. Thus, it is possible to remove noise with high accuracy.

In the electric reaction measuring apparatus according to an aspect of the present disclosure, the at least one control circuit calculates at least two principal components for each of the measurement electrodes; calculates, regarding the potentials corresponding to the principal components, a correlation coefficient of the potentials corresponding to two of the principal components; groups the two principal components whose correlation coefficient is greater than or equal to a predetermined value into one group; calculates, as a contribution ratio of the group, a sum of contribution ratios of all of the principal components included in the group; extracts, regarding the contribution ratio of the group and the contribution ratios of the principal components that are not included in the group, the group and the principal components that are not included in the group in descending order of the contribution ratio; estimates a sum of potentials corresponding to the principal components that are included in the extracted group and in the extracted principal components that are not included in the group; and subtracts the sum of the potentials from the potential measured at the measurement electrode.

With the above aspect, principal components included in the extracted group have a high correlation coefficient and are similar to each other. The sum of potentials, which are composed of potentials corresponding to principal components whose contribution ratios are high, includes potentials corresponding to similar principal components. Thus, a potential corresponding to a principal component whose contribution ratio is low due to phase shift and that may be processed as a noise is included in the sum of potentials together with potentials corresponding to similar principal components, and is subtracted, that is, removed from the potential measured at a measurement electrode. Thus, it is possible to remove noise with high accuracy.

An electric reaction processing method according to an aspect of the present disclosure is a method of processing a potential of each of measurement electrodes, which are respectively disposed in chambers in a culture vessel in each of which a measurement object is disposed, with respect to at least one reference electrode. The method includes: acquiring the potential of each of the measurement electrodes with respect to the at least one reference electrode; calculating at least one principal component for each of the measurement electrodes by performing principal component analysis of the potential of each of the measurement electrodes; estimating, for each of the measurement electrodes, a potential corresponding to the principal component from the principal component of the measurement electrode, and synthesizing the estimated potential; subtracting the synthesized potential of each of the measurement electrodes from the potential acquired for the measurement electrode; and outputting a potential after subtraction. With the above aspect, advantages that are the same as those of the electric reaction measuring apparatus according to an aspect of the present disclosure can be obtained.

A non-transitory computer-readable recording medium according to an aspect of the present disclosure causes a computer to execute a process. The process includes: acquiring a potential between each of measurement electrodes, which are respectively disposed in chambers in a culture vessel in each of which a measurement object is disposed, and at least one reference electrode; calculating at least one principal component for each of the measurement electrodes by performing principal component analysis of the potential for each of the measurement electrodes; estimating, for each of the measurement electrodes, a potential corresponding to the principal component from the principal component of the measurement electrode, and synthesizing the estimated potential; subtracting the synthesized potential of the measurement electrode from the potential acquired for the measurement electrode; and outputting a potential after subtraction. With the above aspect, advantages that are the same as those of the electric reaction measuring apparatus according to an aspect of the present disclosure can be obtained.

General or specific aspects described above may be implemented in a system, a method, an integrated circuit, a computer program, a computer-readable recording medium such as a compact disc-read only memory (CD-ROM), or any appropriate combination of any of these. Examples of the computer readable recording medium include non-volatile recording media, such as a CD-ROM. The apparatus may be constituted by one or more apparatuses. When the apparatus is constituted by two or more apparatuses, the two or more apparatuses may be disposed in one unit or may be disposed in two or more separate units. In the present specification and the claims, the term "apparatus" may mean not only one apparatus but also a system including multiple apparatuses.

Hereafter, an electric reaction measuring apparatus according to the present disclosure will be described in detail with reference to the drawings. Each of embodiments described below shows a general or specific example. Values, shapes, constituent elements, the dispositions of and connections between the constituent elements, steps, and the order of the steps are examples and are not intended to limit the present disclosure. Constituent elements that are described in the embodiments and that are not described in the independent broadest claim are optional elements. The drawings are schematic view and are not necessarily drawn precisely. Moreover, in the drawings, constituent elements that are substantially the same are denoted by the same numerals, and redundant descriptions of such elements may be omitted or simplified.

First Embodiment

An electric reaction measuring apparatus 1 according to a first embodiment will be described. The electric reaction measuring apparatus 1 according to the first embodiment includes measurement electrodes that are electrically separated from each other by a partition wall, a culture vessel including at least one reference electrode, a potential meter including a potential acquirer and a controller, and a processing unit including a memory and a signal processor. In the electric reaction measuring apparatus 1, the potential meter acquires the potentials of each of the measurement electrodes and the reference electrode of the culture vessel. The potential meter may acquire the potentials of the measurement electrodes with respect to the ground potential. The potential meter may acquire the potential of the reference electrode with respect to the ground potential.

Regarding the time waveform of the potential difference, which is the difference between the potential of each of the measurement electrodes with respect to the ground potential and the potential of the reference electrode with respect to the ground potential, the processing unit extracts a time-varying component of a potential difference that is common to the potential differences of the measurement electrodes by using principal component analysis.

Moreover, the processing unit removes the extracted time-varying component of the potential difference as noise from the time waveform of the potential difference of each measurement electrode, thereby reducing noise included in the potential difference of each measurement electrode.

Hereafter, the potential difference between the potential of the measurement electrode and the potential of the reference electrode may be referred to simply as "potential". The time waveform of a potential difference may be referred to as "potential waveform".

1-1. Configuration of Electric Reaction Measuring Apparatus

Figure 2:
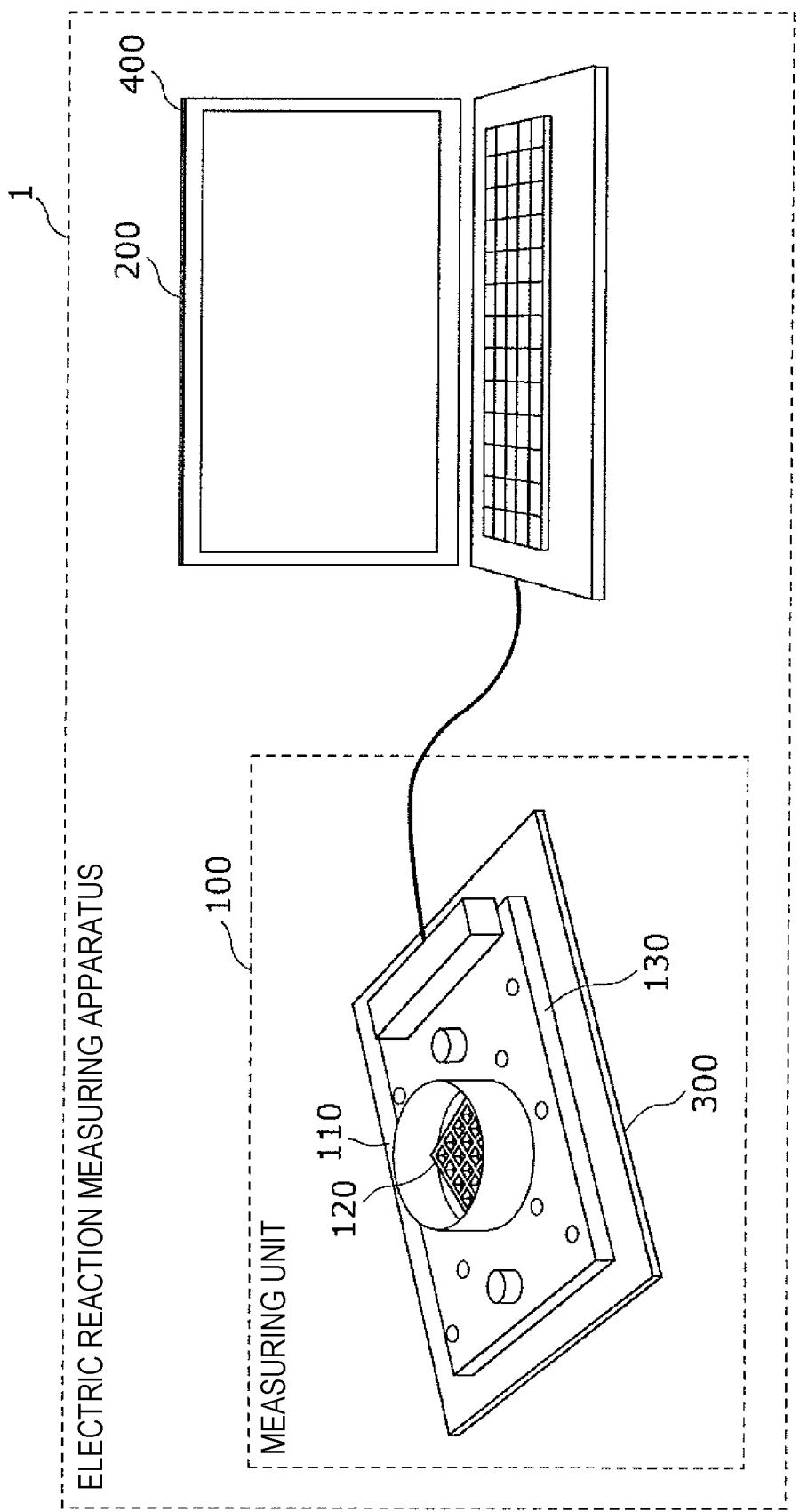
FIG. 2 is a schematic perspective view illustrating an example of the configuration of the electric reaction measuring apparatus according to the first embodiment.

The configuration of the electric reaction measuring apparatus 1 according to the first embodiment will be described. FIG. 1 is a block diagram illustrating an example of the functional configuration of the electric reaction measuring apparatus 1 according to the first embodiment. FIG. 2 is a schematic perspective view illustrating an example of the configuration of the electric reaction measuring apparatus 1 according to the first embodiment. As illustrated in FIG. 1, the electric reaction measuring apparatus 1 includes a measuring unit 100 and a processing unit 200. The processing unit 200 processes data of electric signals measured by the measuring unit 100. The measuring unit 100 includes a culture vessel 110, an electrode 120 in the culture vessel 110, and a potential meter 130. The processing unit 200 includes a memory 210, a signal processor 220, and an output unit 230.

1-1-1. Configuration of Measuring Unit 100

The configuration of the measuring unit 100 will be described. The measuring unit 100 outputs, to the processing unit 200, change in potential due to an electrical reaction of an object in the culture vessel 110. Examples of the object include a biological material such as a cell or tissue. Although this is not a limitation, in the present embodiment, it is assumed that the object is a cultured cell or a cultured tissue cultured in the culture vessel 110. The terms "cell" and "cultured cell" include the meaning of a single cell and multiple cells such as a cell cluster.

Figure 3:
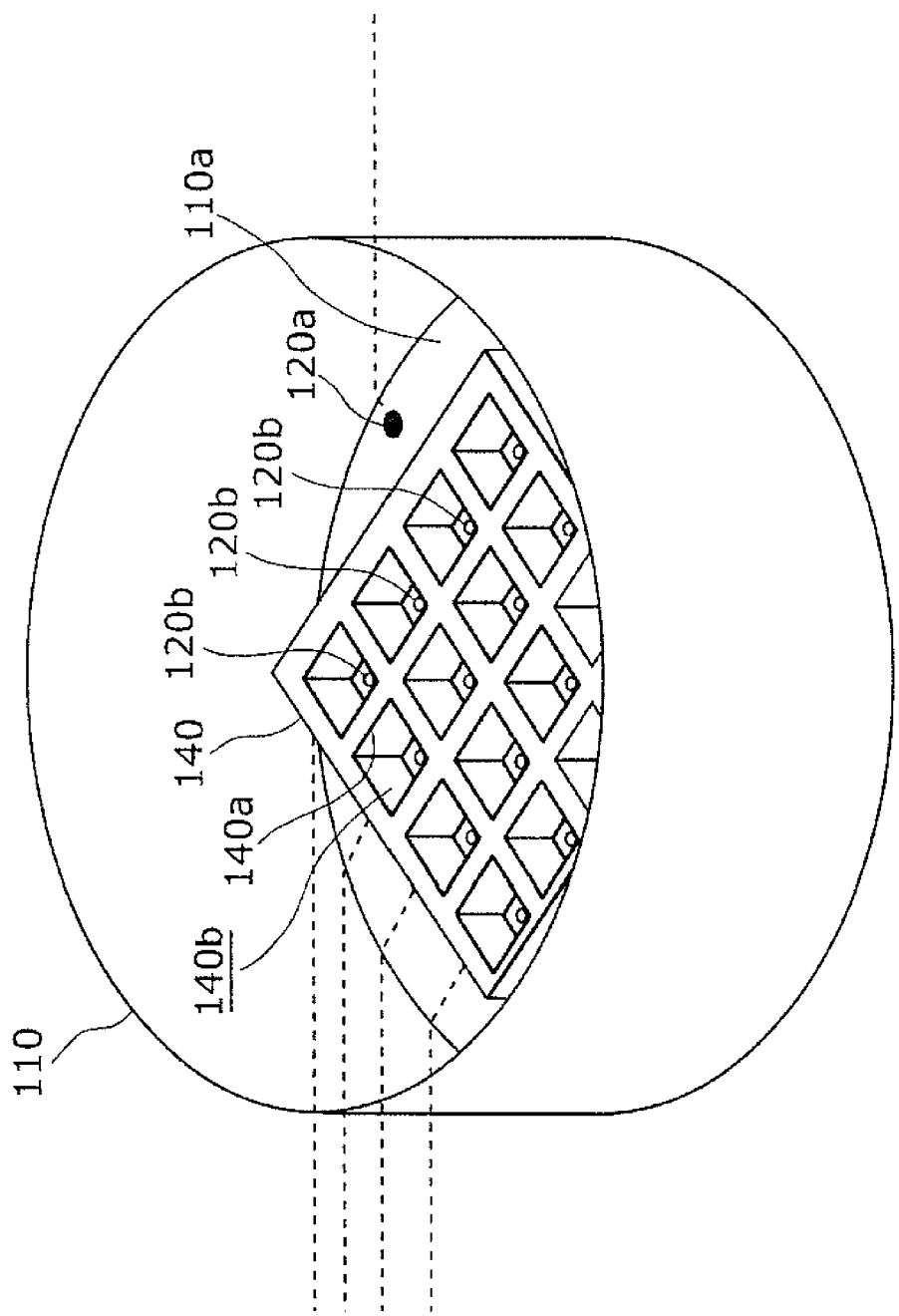
FIG. 3 is a schematic perspective view illustrating an example of the configuration of a culture vessel in FIG. 2.
Figure 4A:
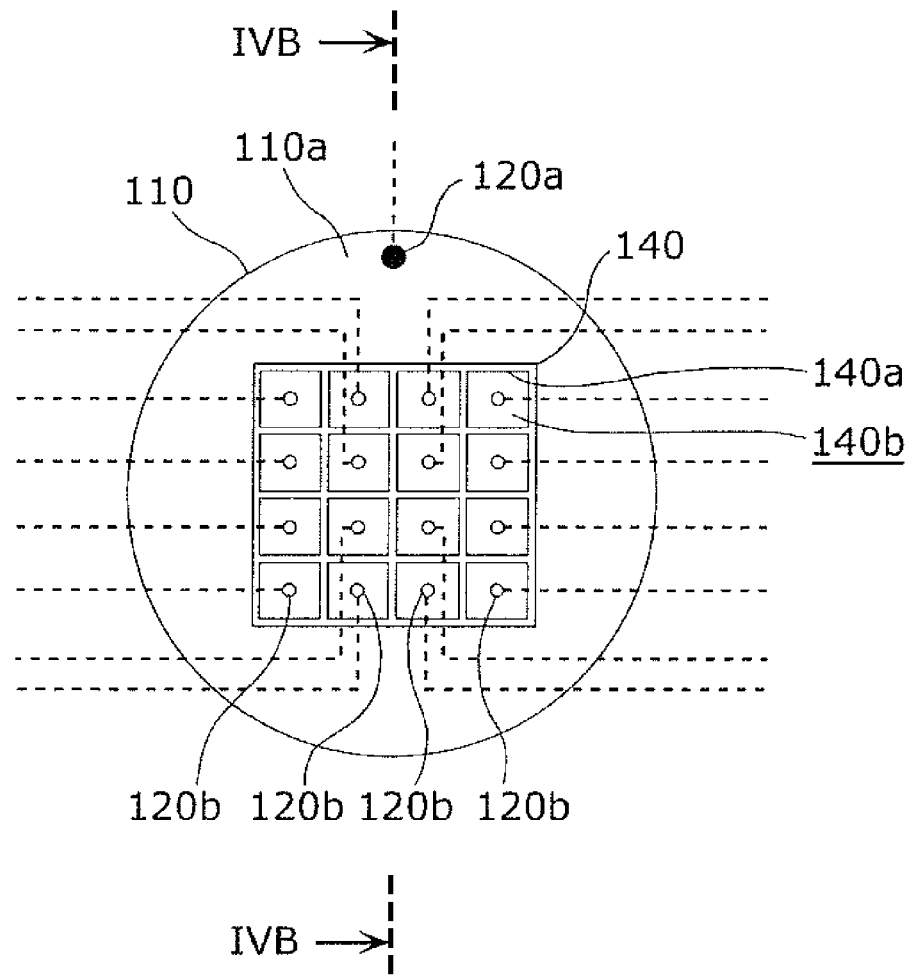
FIG. 4A is a schematic plan view illustrating an example of the configuration of a reference electrode and measurement electrodes in the culture vessel in FIG. 3.
Figure 4B:
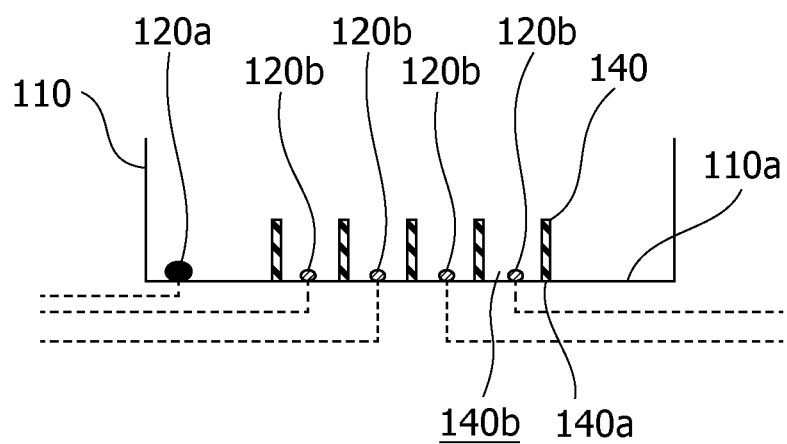
FIG. 4B is a schematic sectional side view taken along line IVB-IVB in FIG. 4A.

Referring to FIGS. 1, 3, 4A, and 4B, the configurations of the culture vessel 110 and the electrode 120 will be described. FIG. 3 is a schematic top perspective view illustrating an example of the configuration of the culture vessel 110 in FIG. 2. FIG. 4A is a schematic plan view illustrating an example of the configuration of a reference electrode 120a and measurement electrodes 120b in the culture vessel 110 in FIG. 3. FIG. 4B is a schematic sectional side view taken along line IVB-IVB in FIG. 4A.

As illustrated in FIG. 3, the culture vessel 110 is a vessel for culturing cells and tissues. The culture vessel 110 holds a culture solution including cells or tissues. In the example illustrated in FIG. 3, the culture vessel 110 is a culture dish having a cylindrical shape with a bottom, which is called a Petri dish. However, the culture vessel 110 may be a culture plate or a culture flask.

As illustrated in FIGS. 3, 4A, and 4B, the culture vessel 110 includes a partition member 140 that is disposed on a bottom wall 110a and that has chambers 140b. The partition member 140 has a partition wall 140a extending in a lattice shape, and the partition wall 140a separates the chambers 140b from each other. The partition wall 140a is disposed so as to surround each chamber 140b. The chamber 140b is a rectangular-parallelepiped hollow space. Since the chamber 140b is also called a "well", in the present specification and in the claims, the chamber 140b may be also referred to as a "well". Cultured cells or tissues are disposed in the wells 140b.

Each well 140b opens downward toward the bottom wall 110a and opens upward in the opposite direction. Each well 140b is physically and electrically separated from another well 140b that is laterally adjacent thereto. The partition member 140 is made of an electrically insulating material such as resin or glass. Therefore, electrical separation between adjacent wells 140b is increased by the partition wall 140a. That is, an electrical reaction is not easily transmitted between adjacent wells 140b. In the present embodiment, the partition member 140, which has a plate-like shape in its entirety, is also called a well plate. The well 140b has a rectangular shape in plan view as seen from above. However, the well 140b may have any appropriate shape, such as a circular shape, an elliptical shape, or a polygonal shape. The culture vessel 110 and the partition member 140 are replaced every time cells or tissues have been cultured. The culture vessel 110 and the partition member 140 may be independent members or may be an integrated member.

As illustrated in FIGS. 1, 3, 4A, and 4B, the electrode 120 is composed of at least one reference electrode 120a and measurement electrodes 120b1, 120b2, 120bk, 120bm (where m is greater than or equal to 2). The measurement electrodes 120b1 to 120bm are connected to circuits that differ from each other. That is, signals of the measurement electrodes 120b1 to 120bm are independently output to a connector 132 of the potential meter 130. The measurement electrodes 120b1 to 120bm will be also referred to as "measurement electrodes 120b". In the present embodiment, one reference electrode 120a is disposed on the bottom wall 110a of the culture vessel 110. The one reference electrode 120a may be a single electrode or may be a group of electrodes.

If there are more than one reference electrodes, a potential waveform may be acquired by using, as the reference potential, one potential that is obtained by electrically connecting the reference electrodes.

If there are more than one reference electrodes, a potential waveform may be acquired by using, as the reference potential, the average of the potentials of the reference electrodes.

The reference electrode 120a extends through the bottom wall 110a, is exposed in the culture vessel 110, and is in contact with the culture solution in the culture vessel 110. The reference electrode 120a is disposed outside of the partition member 140 and is separated from any of the wells 140b by the partition wall 140a. The reference electrode 120a does not make contact with cells or tissues in the wells 140b. The reference electrode 120a need only to be disposed so as to be in contact with the culture solution. Therefore, the reference electrode 120a may be disposed, instead of a position on the bottom wall 110a, at any position in the culture vessel 110 that is in contact with the culture solution and that is outside of the partition member 140, such as a position on a side wall.

As illustrated in FIGS. 3, 4A, and 4B, the measurement electrodes 120b are disposed on the bottom wall 110a of the culture vessel 110. Each measurement electrode 120b is disposed in the well 140b. To be specific, one measurement electrode 120b is disposed in one well 140b. Each measurement electrode 120b extends through the bottom wall 110a and is exposed in the well 140b. Each measurement electrode 120b is in contact with the culture solution in the well 140b, and is in contact with or in proximity to a cell or tissue in the well 140b. The measurement electrode 120b may be disposed, instead of a position on the bottom wall 110a, at any position that is in contact with or in proximity to a cell or tissue in the well 140b and that is in contact with the culture solution. The measurement electrodes 120b and the reference electrode 120a each need only be disposed at a position in contact with a culture medium.

Wires, such as lead wires, extending from the reference electrode 120a and each measurement electrode 120b are connected to the connector 132 of the potential meter 130. Each wire may be embedded in the bottom wall 110a of the culture vessel 110. In this case, when the culture vessel 110 is placed on the connectors 132, the reference electrode 120a and each measurement electrode 120b are electrically connected to the connectors 132.

Figure 4C:
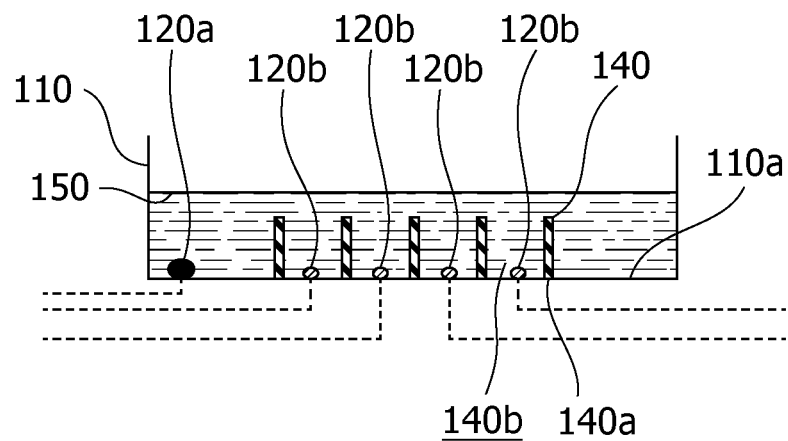
FIG. 4C illustrates a case where the liquid surface of a culture solution is held at a height that exceeds the height of a partition wall.
Figure 4D:
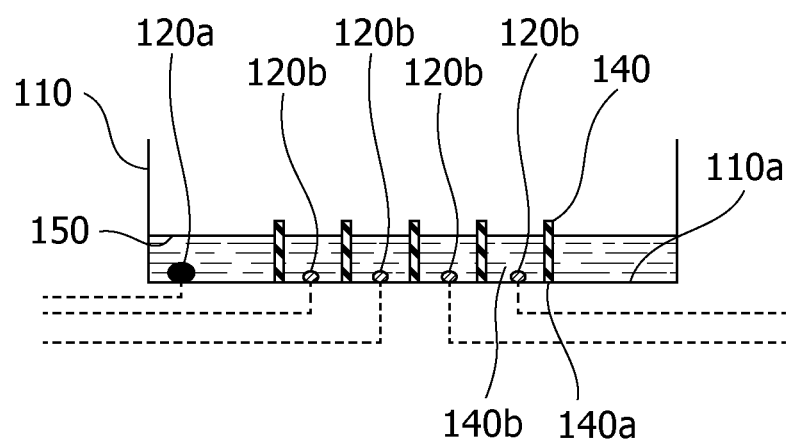
FIG. 4D illustrates a case where the liquid surface of the culture solution is held at a height that does not exceed the height of the partition wall.

The culture solution is held in the culture vessel 110. The liquid surface 150 of the culture solution may be held at a height exceeding the height of the partition wall 140a as illustrated in FIG. 4C, or the liquid surface 150 of the culture solution may be held at a height that does not exceed the height of the partition wall 140a as illustrated in FIG. 4D. When the height of the liquid surface 150 of the culture solution is held at a height exceeding the height of the partition wall 140a as illustrated in FIG. 4C, the measurement electrodes 120b and the reference electrode 120a are electrically connected to each other through the culture solution. However, electrical connection through the culture solution, which circumvents the partition wall 140a having insulating properties, can increase electrical separation between the electrodes by increasing the distance between the electrodes. A cell or tissue is disposed so as to be in contact with or in proximity to the measurement electrode 120b. Compared with the distance between a cell or tissue and a measurement electrode 120b in a well, the distance between the cell or the tissue and a measurement electrode 120b in another well or the reference electrode 120a is sufficiently large, and electrical separation is sufficiently large. Therefore, the probability that an electrical reaction of the cell or the tissue influences potential detection at the measurement electrode 120b in the other well or potential detection at the reference electrode 120a is negligibly low. When the liquid surface 150 of the culture solution is held at a height that does not exceed the height of the partition wall 140a as illustrated in FIG. 4D, the measurement electrodes 120b and the reference electrode 120a are not electrically connected to each other, and electrical separation is sufficiently large.

Figure 5:
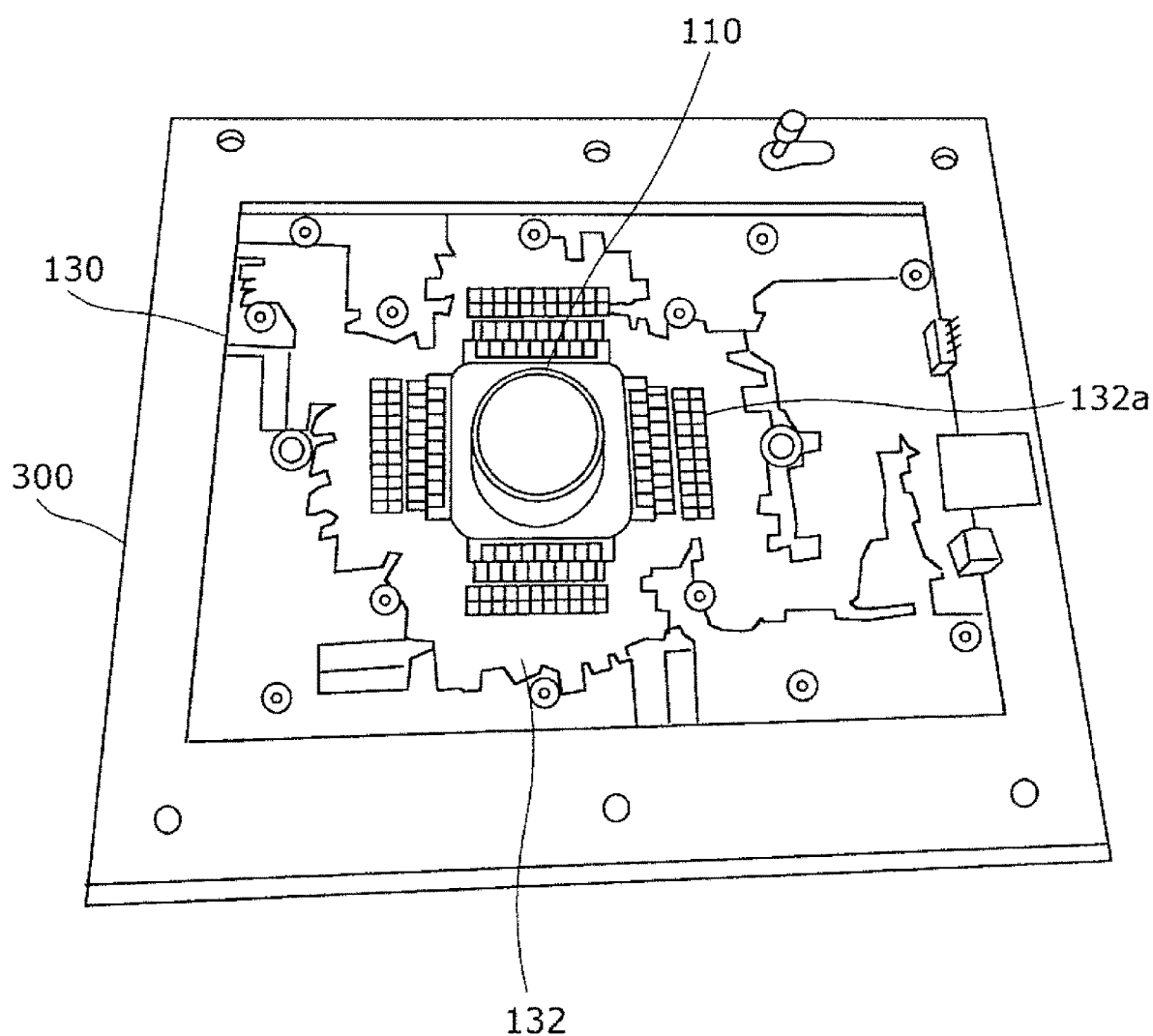
FIG. 5 is a schematic plan view illustrating an example of the configuration of a potential meter of a measuring unit in FIG. 1.

Referring to FIGS. 1, 2, and 5, the configuration of the potential meter 130 will be described. FIG. 5 is a schematic plan view illustrating an example of the configuration of the potential meter 130 of the measuring unit 100 in FIG. 1. The potential meter 130 acquires the potential waveform of cells or tissues that are in contact with or in proximity to the measurement electrodes 120b. As illustrated in FIGS. 1 and 2, the potential meter 130 includes a potential acquirer 131, the connector 132, and a controller 133. In the present embodiment, the potential meter 130 constitutes the entirety or a part of a connector device 300 having a plate-like shape as illustrated in FIG. 2. The connector device 300 is configured so that the culture vessel 110 can be placed on a placement surface thereof, and is connected to a computer 400 via wired or wireless communication. The processing unit 200 constitutes the entirety or a part of the computer 400.

As illustrated in FIGS. 1, 2, and 5, the connector 132 includes terminals 132a disposed on the placement surface of the connector device 300. The connector 132 is composed of the terminals 132a and a circuit connected to the terminals 132a. The terminals 132a are in contact with and electrically connected to wires such as lead wires extending from the reference electrode 120a and the measurement electrodes 120b of the culture vessel 110 placed on the placement surface of the connector device 300. The connector 132 connects the wires, which are respectively connected to the reference electrode 120a and the measurement electrodes 120b, to the circuit in the connector device 300. To be specific, the connector 132 connects the reference electrode 120a and the measurement electrodes 120b to the inside of the potential meter 130, that is, to the potential acquirer 131 by enabling the terminals 132a of the connector 132 to be in contact with the wires.

The potential acquirer 131 acquires the potential difference between the potentials of each measurement electrode 120b of the culture vessel 110, which is connected to the circuit via the connector 132, and the potential of the reference electrode 120a while performing sampling at a predetermined sampling frequency and digitizing the sampled data. In the present specification and the claims, the potential difference between the measurement electrode 120b and the reference electrode 120a may be referred to as "the potential of the measurement electrode 120b".

A cell or tissue that is in contact with or in proximity to the measurement electrode 120b performs an activity such as: an activity that is caused by change in culture environment, such as a chemical change due to addition of a drug, an electric stimulus, or vibration; or an autonomous activity of the cell or tissue. Examples of the autonomous activity include cell division, spontaneous electric discharge, and secretion of a chemical substance. The potential acquirer 131 acquires change in the potential difference between the potential of the measurement electrode 120b and the potential of the reference electrode 120a, which occurs due to the activity. The measurement electrodes 120b are electrically separated from each other by the partition wall 140a of the partition member 140, and the wires extending from the measurement electrodes 120b are insulated from each other. Therefore, change in potential in each well 140b is not easily transmitted to another well 140b and is acquired by the potential acquirer 131 in a state in which an influence on another well 140b and influence from another well 140b are suppressed.

The controller 133 controls the operation of the potential acquirer 131. Moreover, the controller 133 outputs, to the processing unit 200, the value of the potential of each measurement electrode 120b with respect to the potential of the reference electrode at each sampling point, which has been acquired by the potential acquirer 131, and stores the value in the memory 210 of the processing unit 200.

The potential acquirer 131 and the controller 133 may be implemented in a computer system (not shown) that includes a processor such as a central processing unit (CPU) or a digital signal processor (DSP), memories such as a random-access memory (RAM) and a read-only memory (ROM), and the like. Some or all functions of the potential acquirer 131 and the controller 133 may be performed by executing a program, which is stored in the ROM, by using the RAM as a working memory. Some or all functions of the potential acquirer 131 and the controller 133 may be performed by a dedicated hardware circuit, such as an electronic circuit or an integrated circuit. Some or all functions of the potential acquirer 131 and the controller 133 may be configured as a combination of the software function and the hardware circuit

1-1-2. Configuration of Processing Unit 200

Referring to FIGS. 1 and 2, the configuration of the processing unit 200 will be described. The processing unit 200 removes noise common to the measurement electrodes 120b from a measurement result of measuring a potential with respect to the potential of the reference electrode, which is output from the potential meter 130, and outputs a result after noise removal. The processing unit 200 constitutes, for example, a part or the entirety of the computer 400 illustrated in FIG. 2. The processing unit 200 includes the memory 210, the signal processor 220, and the output unit 230. Here, the processing unit 200 is an example of a control circuit.

The memory 210 can store and retrieve various information items. The memory 210 is constituted, for example, by storage devices such as a semiconductor memory such as a ROM, a RAM, or a flash memory; a hard disk drive; and a solid state drive (SSD). The memory 210 stores information that is output from the potential meter 130 to the processing unit 200. To be specific, the potential meter 130 outputs, to the memory 210, the value of a potential with respect to the potential of the reference electrode, which is obtained by sampling the potential of each measurement electrode 120b acquired by the potential acquirer 131 at each sampling point, that is, at each predetermined time. Therefore, the memory 210 stores the value of the potential of each measurement electrode 120b with respect to the potential of the reference electrode at each predetermined time, in association with a measurement time. For example, FIG. 6 illustrates an example of contents stored in the memory 210 of the processing unit 200 in FIG. 1. In the example illustrated FIG. 6, the value of a potential with respect to the potential of the reference electrode, which is measured at each measurement electrode 120b at each time, is stored in the memory 210. Potentials handled by the signal processor 220 and the output unit 230 are potentials with respect to the potential of the reference electrode.

The signal processor 220 removes noise common to the measurement electrodes 120b by performing principal component analysis of a potential waveform composed of the value of the potential of each measurement electrode 120b stored in the memory 210 and the time axis. The detailed configuration of the signal processor 220 will be described below. Constituent elements of the signal processor 220, which will be described below, may be implemented in a computer system (not shown) that includes a processor, such as a CPU or a DSP, memories such as a RAM and a ROM, and the like. Some or all functions of each constituent element may be performed by the CPU or the DSP by executing programs, which are stored in the ROM, by using the RAM as a working memory. Some or all functions of each constituent element may be performed by a dedicated hardware circuit, such as an electronic circuit or an integrated circuit. Some or all functions of each constituent element may be configured as a combination of the software function and the hardware circuit. The program may be stored beforehand in each constituent element, or may be provided as an application through communication via a communication network such as the Internet, communication in accordance with a mobile communication standard, another wireless network, a wired network, or broadcasting.

The output unit 230 outputs a signal of a potential waveform of each measurement electrode 120b from which noise has been removed by the signal processor 220. An example of the output signal is data of the potential waveform of each measurement electrode 120b represented as a numeric series. The output unit 230 may output and store the output signal in a storage medium (not shown). Alternatively, the output unit 230 may output the output signal to a display or a printer to cause display to display the output signal or to cause the printer to print the output signal on a print medium such as paper. Alternatively, the output unit 230 may output the output signal to software or a circuit that performs a determination process on the output signal. An example of the determination is determination of whether the activity of a cell or tissue is good, which is performed based on the potential waveform. The output unit 230 may be constituted by a circuit that outputs a signal to an output target.

Referring to FIG. 1, the detailed configuration of the signal processor 220 will be described. Concerning the potential of each measurement electrode 120b at each predetermined time stored in the memory 210, that is, the potential waveform on the time axis, the signal processor 220 regards the potential waveforms of the measurement electrodes 120b as a data series of variables at each sample point. To be specific, the data series includes variables X1 to Xm, and the variables X1 to Xm are respectively potentials in the potential waveforms of the measurement electrodes 120b1 to 120bm at the sample point of the same time. For example, a value $Xkl$ (l=1 to p, l: integer) of the variable Xk (k=1 to m, m: integer) corresponds to a potential at a specific sample point l in the potential waveform of the measurement electrode 120bk. A potential at a sample point is, for example, a potential measured at each predetermined time. The variable Xk can be represented by a vector having Xkl (l=1 to p, l: integer) as elements, and hereafter, may be referred to as a variable Xk vector. That is, the notation may be as follows: X1=(X11 . . . X1l . . . X1p), Xk=(Xk1 . . . Xkl . . . Xkp), . . . Xm=(Xm1 . . . Xml . . . Xmp). Here, when the sampling period is denoted by "a", X11 is the potential of the measurement electrode 120b1 measured at a time t, . . . , X1l is the potential of the measurement electrode 120b1 measured at a time t+(l−1)×a, . . . , X1p is the potential of the measurement electrode 120b1 measured at a time t+(p−1)×a; . . . ; Xk1 is the potential of the measurement electrode 120bk measured at a time t, . . . , Xkl is the potential of the measurement electrode 120bk measured at a time t+(l−1)×a, . . . , Xkp is the potential of the measurement electrode 120bk measured at a time t+(p−1)×a; . . . ; and Xm1 is the potential of the measurement electrode 120bm measured at a time t, . . . , Xml is the potential of the measurement electrode 120bm measured at a time t+(l−1)×a, . . . , Xmp is the potential of the measurement electrode 120bm measured at a time t+(p−1)×a.

Moreover, the signal processor 220 extracts a component common to the potential waveforms of the measurement electrodes 120b1 to 120bm as a principal component by performing principal component analysis of data series composed of the variables X1 to Xm. The signal processor 220 regards the principal component common to the measurement electrodes 120b1 to 120bm as noise.

To be specific, the signal processor 220 regards potentials respectively recorded at the measurement electrodes 120b1 to 120bm as respective data series, performs principal component analysis of data including the data series, and thus extracts and calculates at least one principal component for each measurement electrode 120b1 to 120bm. Moreover, for each of the measurement electrode 120b1 to 120bm, the signal processor 220 estimates, from the principal component of the measurement electrode, a potential corresponding to the principal component. That is, for each extracted principal component, the signal processor 220 estimates a potential due to the principal component for each measurement electrode 120bk (k=1 to m) in accordance with coefficients for the variables X1 to Xm (referred to as "principal component coefficients"), which are data acquired at the measurement electrodes 120b1 to 120bm, and a principal component scores at each measurement time, that is, each sample point.

Moreover, the signal processor 220 synthesizes the estimated potential of each measurement electrode 120bk due to the principal component, and subtracts the synthesized potential of the measurement electrode 120bk from the potential measured at the measurement electrode 120bk. The signal processor 220 outputs the remainder of subtraction, which has been calculated for each measurement electrode 120bk, as a noise removal result of the measurement electrode 120bk. Note that, for example, the principal component score $z_i$ of the i-th principal component, among multiple principal components, can be represented as $z_i = a_{i1} \times X1 + a_{i2} \times X2 + \ldots + a_{im} \times Xm$, where X1 to Xm are variables, and $a_{i1}$ to $a_{im}$ are the principal component coefficients for the variables X1 to Xm.

$(Zi1 \ldots Zil \ldots Zip)^T = a_{i1} \times (Xm1 \ldots Xml \ldots Xmp)^T + \ldots + a_{im} \times (Xm1 \ldots Xml \ldots Xmp)^T$, where $X1=(X11 \ldots X1l \ldots X1p), \ldots, Xm=(Xm1 \ldots Xml \ldots Xmp)$.

The signal processor 220 includes a principal component analyzer 221, a principal component synthesizer 222, and a common noise remover 223. The principal component analyzer 221 performs principal component analysis by generating a covariance matrix or a correlation matrix between all measurement electrodes for the value of the potential of each measurement electrode 120bk (k=1 to m) stored in the memory 210. The principal component analyzer 221 continues extraction of principal components until a predetermined number of principal components are extracted. Alternatively, the principal component analyzer 221 continues extraction of principal components until the contribution ratio, to the total variance, of the extracted principal components, that is, the cumulative contribution ratio of the extracted principal components exceeds a predetermined value. That is, the principal component analyzer 221 calculates, for each principal component, the contribution ratio of the principal component to the variance of all measured potentials, and extracts some of the principal components in descending order of the contribution ratio.

The term "contribution ratio" of a principal component refers to the proportion, in the entire information of data, of information represented by the eigenvalue of the principal component, and is the ratio of the eigenvalue to the total variance. The cumulative contribution ratio is a value calculated by adding the contribution ratios of the principal components in descending order. An example of the value of the predetermined cumulative contribution ratio is 70%. The principal component analyzer 221 outputs, to the principal component synthesizer 222, the principal component coefficient and the principal component score of each of the extracted principal components. The total variance is the variance of data measured at all measurement electrodes used in principal component analysis.

The number of measurement electrodes corresponds to the dimension of data in principal component analysis. Therefore, for example, in principal component analysis, the number of principal components that can be obtained is the same as the number of the variables X1 to Xm of the data series. For example, the first principal component is a linear combination of variables that has the largest variance among all linear combinations of the variables. The second principal component is a linear combination that is uncorrelated with the first principal component and that has the largest variance among the linear combinations. Likewise, the third principal component and the following principal components are each a linear combination that is uncorrelated with the previous principal components and that has the largest variance among the linear combinations. That is, as linear combinations of variables, orthogonal components converted in descending order of variance are obtained as principal components. An eigenvalue obtained by principal component analysis is the variance of principal component. An eigenvector obtained by principal component analysis is a vector whose elements are principal component coefficients that are weights by which the variables X1 to Xm are multiplied when representing a principal component by using the variables X1 to Xm. A principal component score is the linear combination of the eigenvector and the variables X1 to Xm. Details of the principal component analysis will be described below.

The principal component analysis may be performed as follows. The principal component analyzer 221 obtains $avg1=(X11+ \ldots +Xk1+ \ldots +Xm1)/m$, which is the average of potentials at a time t, $avgl=(X1l+ \ldots +Xkl+ \ldots +Xml)/m$, which is the average of potentials at a time $t+(l-1) \times a$, $avgp=(X1p+ \ldots +Xkp+ \ldots +Xmp)/m$, which is the average of potentials at a time $t+(p-1) \times a$.

The principal component analyzer 221 obtains the covariance matrix V for the variable $X1=(X11, \ldots, X1l, \ldots, X1p), \ldots$, variable $Xk=(Xk1, \ldots, Xkl, \ldots, Xkp), \ldots$, variable $Xm=(Xm1, \ldots, Xml, \ldots, Xmp)$.

Next, the principal component analyzer 221 obtains an eigenvalue $\lambda 1$, an eigenvalue $\lambda 2, \ldots$, an eigenvalue $\lambda m$ of the covariance matrix.

Then, the principal component analyzer 221 obtains, from the eigenvalues $\lambda 1, \lambda 2, \ldots, \lambda m$, the eigenvector $(u1_{max1} \; u2_{max1} \; \ldots \; um_{max1})^T$ of the largest eigenvalue $\lambda max1$, the eigenvector $(u1_{max2} \; u2_{max2} \; \ldots \; um_{max2})^T$ of the second largest eigenvalue $\lambda max2, \ldots$.

The principal component analyzer 221 "continues extraction of principal components until the cumulative contribution ratio of the extracted principal components exceeds a predetermined value". An example of this process is as follows.

For example, the covariance matrix for X1=(X11, X12, X13), X2=(X21, X22, X23), and X3=(X31, X32, X33) is $$\begin{pmatrix} \sum_{\alpha=1}^{3}(X\alpha 1-avg1)(X\alpha 1-avg1)/3 & \sum_{\alpha=1}^{3}(X\alpha 1-avg1)(X\alpha 2-avg2)/3 & \sum_{\alpha=1}^{3}(X\alpha 1-avg1)(X\alpha 3-avg3)/3 \\ \sum_{\alpha=1}^{3}(X\alpha 2-avg2)(X\alpha 1-avg1)/3 & \sum_{\alpha=1}^{3}(X\alpha 2-avg2)(X\alpha 2-avg2)/3 & \sum_{\alpha=1}^{3}(X\alpha 2-avg2)(X\alpha 3-avg3)/3 \\ \sum_{\alpha=1}^{3}(X\alpha 3-avg3)(X\alpha 1-avg1)/3 & \sum_{\alpha=1}^{3}(X\alpha 3-avg3)(X\alpha 2-avg2)/3 & \sum_{\alpha=1}^{3}(X\alpha 3-avg3)(X\alpha 3-avg3)/3 \end{pmatrix},$$

where avg1=(X11+X21+X31)/3, which is the average of potentials at a time t, avg2=(X12+X22+X32)/3, which is the average of potentials at a time t+a, and avg3=(X13+X23+X33)/3, which is the average of potentials at a time t+2a.

The eigenvalues of the covariance matrix V obtained by the principal component analyzer 221 will be denoted by $\lambda 1$, $\lambda 2$, and $\lambda 3$; and the eigenvector for the eigenvalue $\lambda 1$ will be represented as $$\vec{u1} = (u11 \; u12 \; u13)^T, \text{ and}$$

the eigenvector for the eigenvalue $\lambda 2$ will be represented as $$\vec{u2} = (u21 \; u22 \; u23)^T.$$

Here, if the cumulative contribution ratio is 70%, $\lambda 1 > \lambda 2 > \lambda 3$, $(\lambda 1/\text{sum}) < (70/100)$, and $\{(\lambda 1 + \lambda 2)/\text{sum}\} > (70/100)$, the principal component analyzer 221 obtains a first principal component score z1 and a second principal component score z2. That is, the principal component analyzer 221 need not obtain a third principal component score z3, which uses elements of the eigenvector for the eigenvalue $\lambda 3$.

Note that z1l=u11×X1l+u12×X2l+u13×X3l, (1≤l≤p); z2l=u21×X1l+u22×X2l+u23×X3l, (1≤l≤p); and $$\text{sum} = \sum_{\alpha=1}^{3} \frac{(X\alpha 1-avg1)(X\alpha 1-avg1)}{3} + \sum_{\alpha=1}^{3} \frac{(X\alpha 2-avg2)(X\alpha 2-avg2)}{3} + \sum_{\alpha=1}^{3} \frac{(X\alpha 3-avg3)(X\alpha 3-avg3)}{3}.$$

The principal component synthesizer 222 synthesizes, based on the principal component coefficients and the principal component scores of the principal components extracted by the principal component analyzer 221, change in potential explained by the extracted principal components for each measurement electrode 120bk (k=1 to m). That is, the principal component synthesizer 222 synthesizes, for each measurement electrode 120bk (k=1 to m), potentials corresponding to extracted principal components. The synthesized waveform, which is a potential waveform, differs between the measurement electrodes 120bk. This is because, the same noise component influences the potentials obtained at the measurement electrodes 120bk in different ways, depending on the resistance of each measurement electrode 120bk, the distance and positional relationship between each measurement electrode 120bk and a noise source, the distance and positional relationship between each measurement electrode 120bk and the reference electrode 120a, and the like. The synthesized waveform based on the principal components of each measurement electrode 120bk represents a noise component that takes the influence of noise on the measurement electrode 120bk into consideration, and is a noise component common to the measurement electrodes 120b1 to 120bm. Thus, the noise component common to the measurement electrodes 120b1 to 120bm can be obtained for each measurement electrode 120bk while taking the influence of noise on the measurement electrode 120bk into consideration.

In the above example, eigenvectors $\vec{pu1}, \vec{u2}$ are principal components, and principal component coefficients of the first principal component are u11, u12, and u13.

Here, the details of the synthesizing process performed by the principal component synthesizer 222 will be described. As described above, the variable Xk (1≤k≤m, k: integer) is a time direction vector of potentials measured at the measurement electrode 120bk (1≤k≤m, k: integer). In the principal component analysis, the i-th principal component (1≤i≤m, i: integer) is one of the principal components extracted by performing principal component analysis on the variables X1 to Xm and that is extracted in the i-th order in descending order of contribution ratio. Note that, when i=m, the entirety of the variance of data is explained by the principal components. Therefore, it is necessary that i<m so that data that is characteristic to the measurement electrodes 120b1 to 120bm can be left as a residue after removing principal components as a noise common to the measurement electrodes 120b1 to 120bm.

Here, the principal component coefficient of the i-th principal component will be denoted by "ai", and the principal component coefficient of the variable Xk will be denoted by "aik". The principal component score of the i-th principal component will be denoted by "zi". In calculation of the principal component score zi, as represented by expression (1) below, for each of extracted principal components, data composed of the coordinates values of the variables X1 to Xm at each sample point, which are disposed in an m-dimensional space having the elements of the vector of the variables X1 to Xm as coordinates, is converted into a value in a space having the principal components as coordinates. Here, the coordinates composed of data (potentials) of the measurement electrodes 120b1 to 120bm at a sample point l (1≤l≤p, l: integer) are denoted by (X1l, X2l, X3l, . . . , Xkl, . . . , Xml).

$$z_{il} = \sum_{k=1}^{m} a_{ik} \times X_{kl} \quad (1)$$

The total variance of data is the variance of the data at all sample points having coordinates (X1l, X2l, X3l, . . . Xkl, . . . , Xml) in the space having the elements of the vector of the variables X1 to Xm as coordinates. In principal component analysis, a data space is set by using the vector of variables X1 to Xm as orthogonal coordinates, and the variance of data is maximized by rotating the coordinate axes, that is, calculation is performed so as to extract axes that optimally explain the variation of the data. Contribution ratio to variance refers to the ratio of variance that can be explained by a principal component to the variation in the m-dimensional data space.

Synthesizing of potential waveforms at the measurement electrode 120$bk$ (on the variables Xk axis) due to the i-th principal component can be explained as follows. That is, a first synthesized waveform Yik at the measurement electrode 120$bk$ due to the i-th principal component can be obtained by multiplying each element of the series of the principal component score zi of the i-th principal component by the principal component coefficient aik of the i-th principal component for the variables Xk, and, further, by adding the average of the elements Xkl (l=1–p) of the variable Xk vector. To be specific, a value Yikl on the first synthesized waveform Yik at a sample point l can be obtained by using expression (2) below. From the value Yik at each sample point l, the first synthesized waveform Yik at the measurement electrode 120$bk$ due to the i-th principal component is generated.

$$Y_{ikl} = z_{il} \times a_{ik} + \frac{\sum_{l=1}^{p} X_{kl}}{p} \quad (2)$$

A second synthesized waveform Yk, which is a potential waveform obtained by synthesizing the 1st to n-th principal components (1≤i≤n, i: integer, n<m) at the measurement electrode 120$bk$, can be obtained by adding the first synthesized waveforms Y1k to Ynk. To be specific, a value (potential) Ykl on the second synthesized waveform Yk at a sample point l is obtained by using expression (3) below. The value Ykl represents "noise" due to the 1st to n-th principal components at the sample point l. The second synthesized waveform Yk, which is formed from the value Ykl at each sample point l, represents "noise" at the measurement electrode 120$bk$ due to the 1st to n-th principal components. The noise is a noise component common to the measurement electrodes 120$b1$ to 120$bm$.

$$Y_{kl} = \sum_{i=1}^{n} Y_{ikl} \quad (3)$$

As described above, the principal component synthesizer 222 calculates, for each measurement electrode 120$bk$ (k=1 to m), the value Yik in the first synthesized waveform due to the i-th principal component at each sample point l by multiplying the element of the series of the principal component score zi of the i-th principal component by the principal component coefficient aik of the i-th principal component for the variable Xk, and by adding the average of the elements of the variable Xk. Moreover, the principal component synthesizer 222 calculates, for each measurement electrode 120$bk$ (k=1 to m), the value Ykl in the second synthesized waveform due to the 1st to n-th principal components at each sample point l by adding the value Yikl in the first synthesized waveform due to the 1st to n-th principal components at the sample point l. Thus, the principal component synthesizer 222 calculates the second synthesized waveform for each measurement electrode 120$bk$ (k=1 to m) due to the 1st to n-th principal components.

The common noise remover 223 obtains, for each measurement electrode 120$bk$, a remainder waveform by subtracting the synthesized waveform (the second synthesized waveform) of change in potential of the measurement electrode 120$bk$ due to the extracted principal components, which has been synthesized by the principal component synthesizer 222, that is, noise from the measured potential waveform of the measurement electrode 120$bk$. The remainder waveform represents a potential waveform after removal of noise at the measurement electrode 120$bk$. If the number of principal components extracted by the principal component analyzer 221 is one, the principal component synthesizer 222 obtains the first synthesized waveform and need not obtain the second synthesized waveform.

Figure 7A:
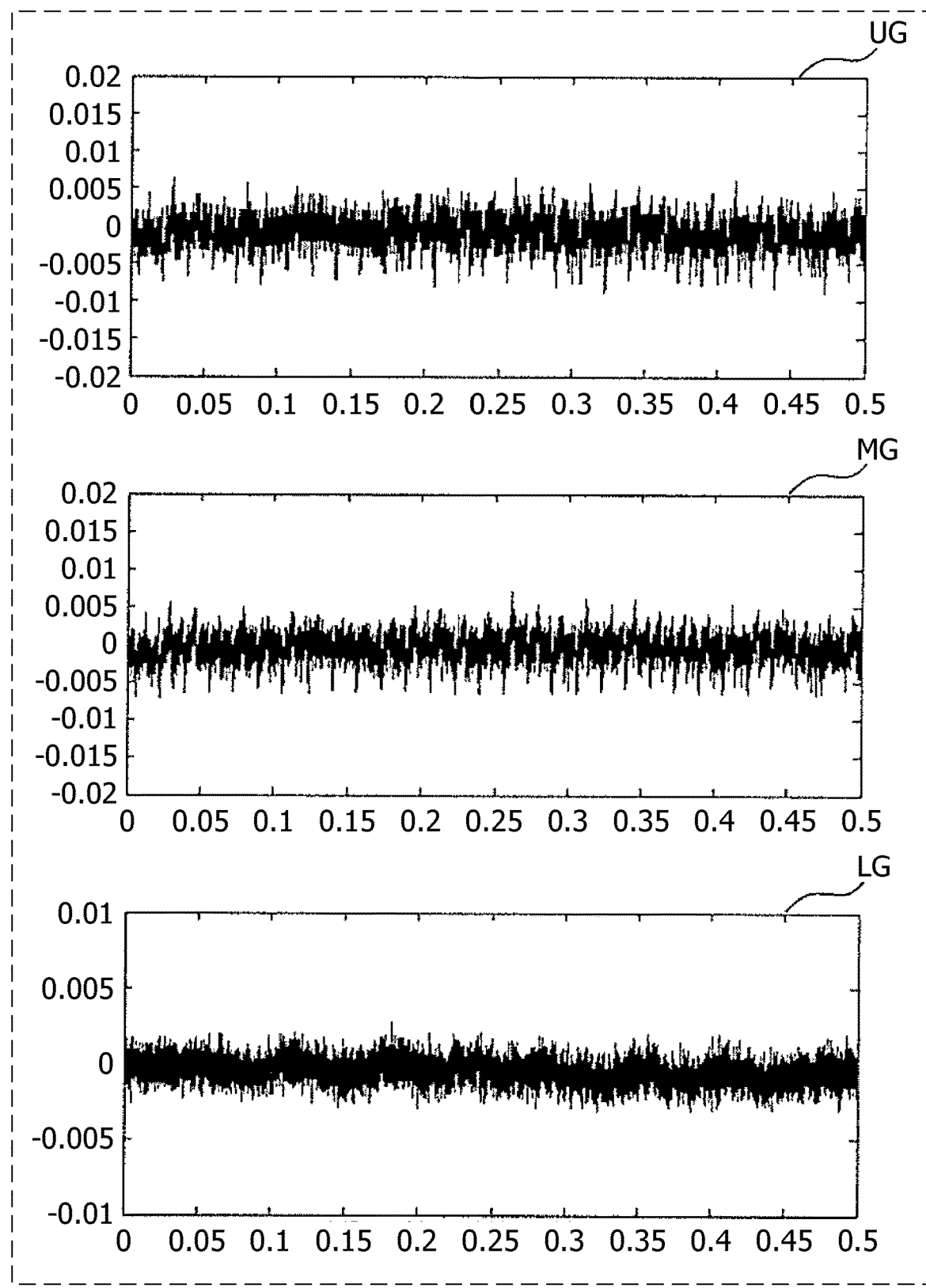
FIG. 7A illustrates an example of a process through which a signal processor of the processing unit in FIG. 1 processes a potential waveform.
Figure 7B:
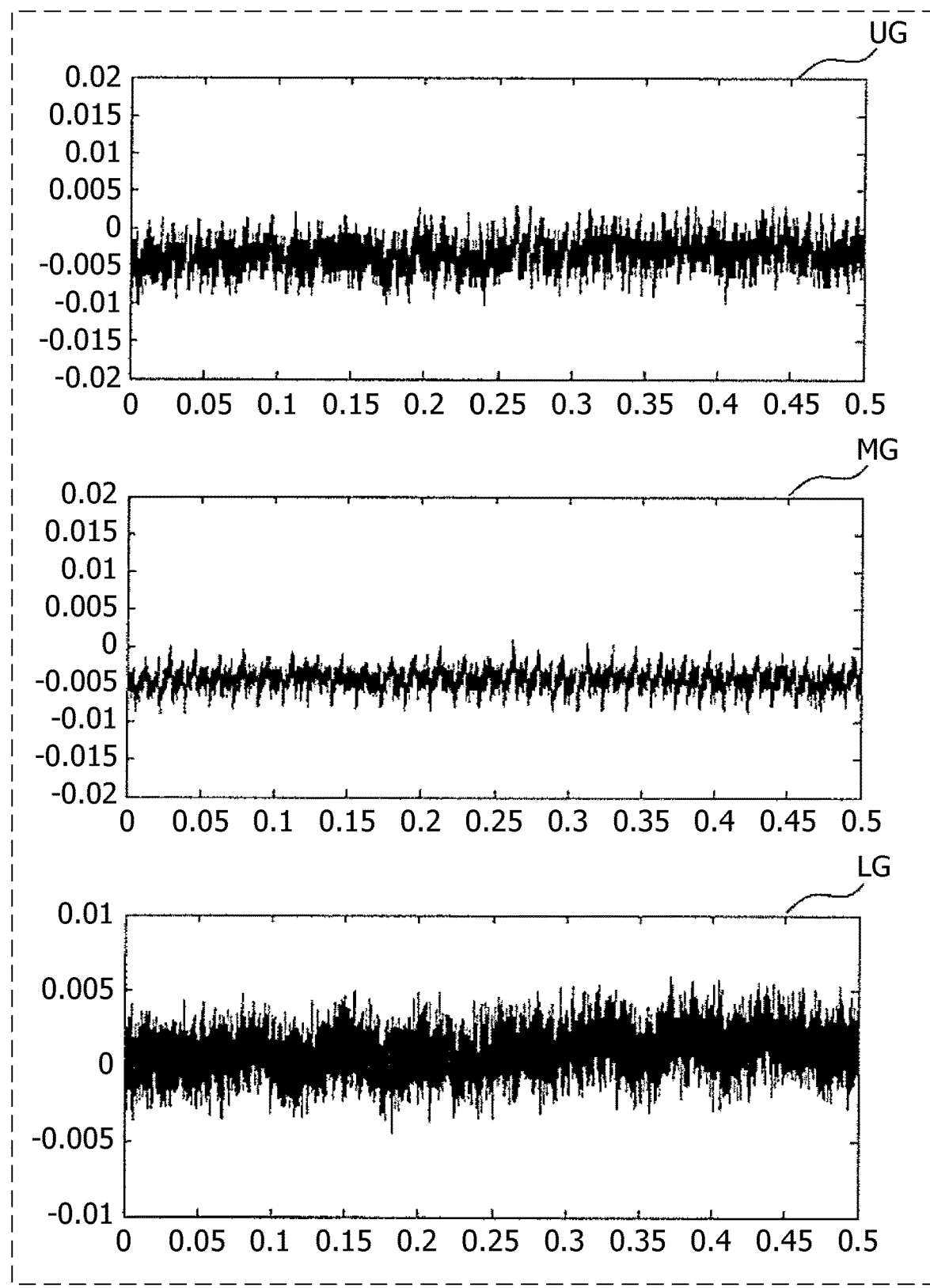
FIG. 7B illustrates an example of a process through which the signal processor of the processing unit in FIG. 1 processes a potential waveform.
Figure 7C:
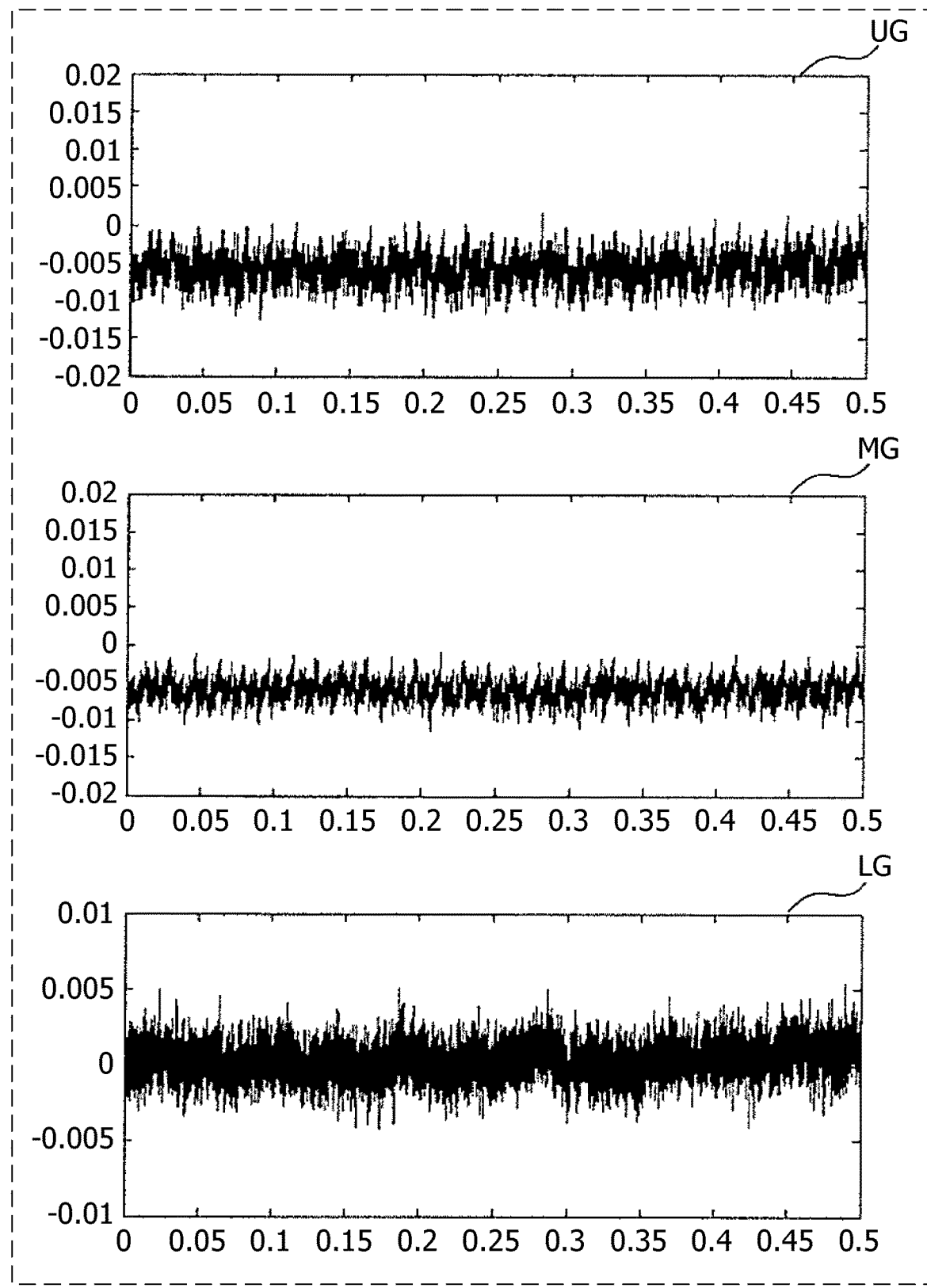
FIG. 7C illustrates an example of a process through which the signal processor of the processing unit in FIG. 1 processes a potential waveform.

For example, FIGS. 7A to 7C illustrate an example of a process through which the signal processor 220 of the processing unit 200 in FIG. 1 processes a potential waveform. FIGS. 7A to 7C illustrate processes through which potential waveforms of three measurement electrodes, among five measurement electrodes 120$bk$ to 120$bk$+4 used for calculation, are processed. To be specific, FIG. 7A illustrates a process for the measurement electrode 120$bk$, FIG. 7B illustrates a process for the measurement electrode 120$bk$+1, and FIG. 7C illustrates a process for the measurement electrode 120$bk$+2. In each of the graphs of FIGS. 7A to 7C, the vertical axis represents potential ($\lambda$V) and the horizontal axis represents time (seconds). In each of the graphs of FIGS. 7A to 7C, an upper graph UG shows a potential waveform before being processed. A middle graph MG shows a noise component that is synthesized by using the first to third principal components extracted by performing principal component analysis. That is, the noise component corresponds to the second synthesized waveform when n=3, which has been described above regarding the principal component synthesizer 222. A lower graph LG shows a potential waveform obtained as a result of removing the noise component shown in the middle graph MG from the potential waveform in the upper graph before being processed. The noise components shown in middle graphs MG, which differ between measurement electrodes in size and in waveform, each include a pulse-shaped periodic component. The pulse frequency of the periodic component is 60 Hz, and the waveform of the pulse sharply varies. As a result of removing the noise component, the lower graphs LG show gentle waveforms that differ between measurement electrodes, which are difficult to be discerned in the upper graphs UG.

1-2. Operation of Electric Reaction Measuring Apparatus

Figure 8:
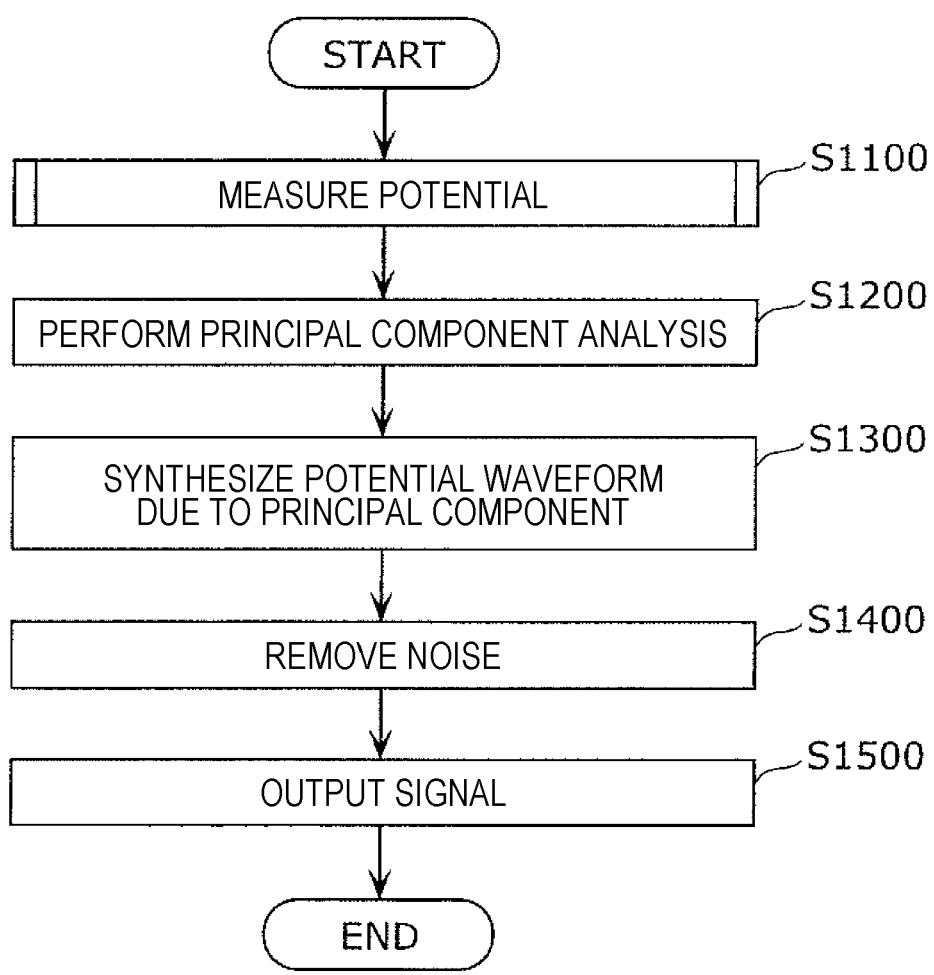
FIG. 8 is a flowchart illustrating an example of an operation performed by the electric reaction measuring apparatus according to the first embodiment.

Next, an operation of the electric reaction measuring apparatus 1 according to the first embodiment will be described. FIG. 8 is a flowchart illustrating an example of an operation performed by the electric reaction measuring apparatus 1 according to the first embodiment.

(Step S1100) First, the measuring unit 100 simultaneously acquires the potentials of the measurement electrodes 120$b1$ to 120$bm$ and the potential of the reference electrode 120$a$. Moreover, the measuring unit 100 acquires the difference between the potential of each of the measurement electrodes 120$b1$ to 120$bm$ and the potential of the reference electrode 120$a$ as the potential of each of the measurement electrodes 120$b1$ to 120$bm$ at predetermined time intervals. The measuring unit 100 stores, in the memory 210 of the processing unit 200, the acquired potential and the acquired time in correspondence with each other for each of the measurement electrodes 120$b1$ to 120$bm$. FIG. 6 shows an example of the contents stored in the memory 210.

(Step S1200) Next, the principal component analyzer 221 of the processing unit 200 sets variables X1 to Xm for a potential waveform that is a time waveform representing the relationship between the potential and the time for each measurement electrode 120*b*1 to 120*bm* stored in the memory 210 in step S1100. Moreover, the principal component analyzer 221 determines, for each of the variables X1 to Xm, potentials at predetermined measurement intervals or potentials at predetermined measurement times in the potential waveform corresponding to the variable as the observed value of the variable, that is, the data value. Thus, the variables X1 to Xm are respectively data series including the potentials of the measurement electrodes 120*b*1 to 120*bm* as data values. The principal component analyzer 221 performs principal component analysis by using the variables X1 to Xm and the data series.

To be specific, the principal component analyzer 221 continues principal component analysis until a predetermined number of principal components are extracted or until principal components whose contribution ratios exceed a predetermined contribution ratio to the total variance are extracted. Calculation of the principal component analysis is performed by using a general calculation method. For example, the principal component analyzer 221 obtains the covariance matrix of potentials for the data series of the variables X1 to Xm of all measurement electrodes 120*b*1 to 120*bm*, and further obtains the eigenvectors and the eigenvalues of the covariance matrix. Here, m eigenvalues and eigenvectors respectively corresponding to the m eigenvalues are calculated. The principal component analyzer 221 sorts the eigenvectors in descending order of eigenvalues, and regards the elements of the eigenvectors as the coefficient series of a principal component. For example, the elements of an eigenvector corresponding to the largest eigenvalue is the coefficient series of the first principal component, and the elements of an eigenvector corresponding to the k-th largest eigenvalue is the coefficient series of the k-th principal component.

When extracting a predetermined number of principal components, the principal component analyzer 221 extracts a predetermined number of principal components in descending order of eigenvalue. When the principal component analyzer 221 determines the number of principal components to be extracted based on the contribution ratios to the total variance, that is, the cumulative contribution ratio, the principal component analyzer 221 obtains the contribution ratios and the cumulative contribution ratio by using the eigenvalues, and extracts a number of principal components that provide the smallest cumulative contribution ratio that exceeds a predetermined cumulative contribution ratio. The principal component analyzer 221 regards the elements of an eigenvector corresponding to a principal component as a principal component coefficient. The principal component analyzer 221 maps individual data, that is, potential data at each sample point with each measurement electrode as an axis onto a principal component axis that is a directional axis of the eigenvector of the obtained principal component, and obtains a value at each sample point on the principal component axis as a principal component score.

(Step S1300) For a predetermined number of principal components extracted in step S1200, the principal component synthesizer 222 obtains, for each measurement electrodes 120*b*1 to 120*bm*, potentials due to the principal components for each measurement time, that is, for each sample point by using the principal component coefficients and the principal component scores, and synthesizes a noise waveform due to the extracted principal components. In synthesizing the potential waveform, potentials at the same sample point in each potential waveform are added.

(Step S1400) The common noise remover 223 obtains a remainder by subtracting the noise waveform due to the principal components of each of the measurement electrodes 120*b*1 to 120*bm* synthesized in step S1300 from the potential waveform representing observed values of each of the measurement electrodes 120*b*1 to 120*bm*. That is, the common noise remover 223 subtracts, from the potential waveform of each measurement electrode 120*bk* (k=1 to m), the noise waveform of the same measurement electrode 120*bk*. A potential generated by the principal components is regarded as a noise common to the measurement electrodes 120*b*1 to 120*bm*, and the noise is subtracted from the observed value, and thereby noise included in the observed values is removed. With such calculation, the common noise remover 223 calculates, for each of the measurement electrodes 120*b*1 to 120*bm*, a time waveform of potential composed of residues calculated at measurement intervals or at measurement times, and thus generates a potential waveform after noise removal at each of the measurement electrodes 120*b*1 to 120*bm*.

(Step S1500) The output unit 230 outputs the potential waveform after noise removal of each of the measurement electrodes 120*b*1 to 120*bm*, which has been calculated by the common noise remover 223 in step S1400, as a numeric series in which a potential is paired with the time when the potential is measured.

1-3. Configuration and Operation of Potential Meter

Figure 9:
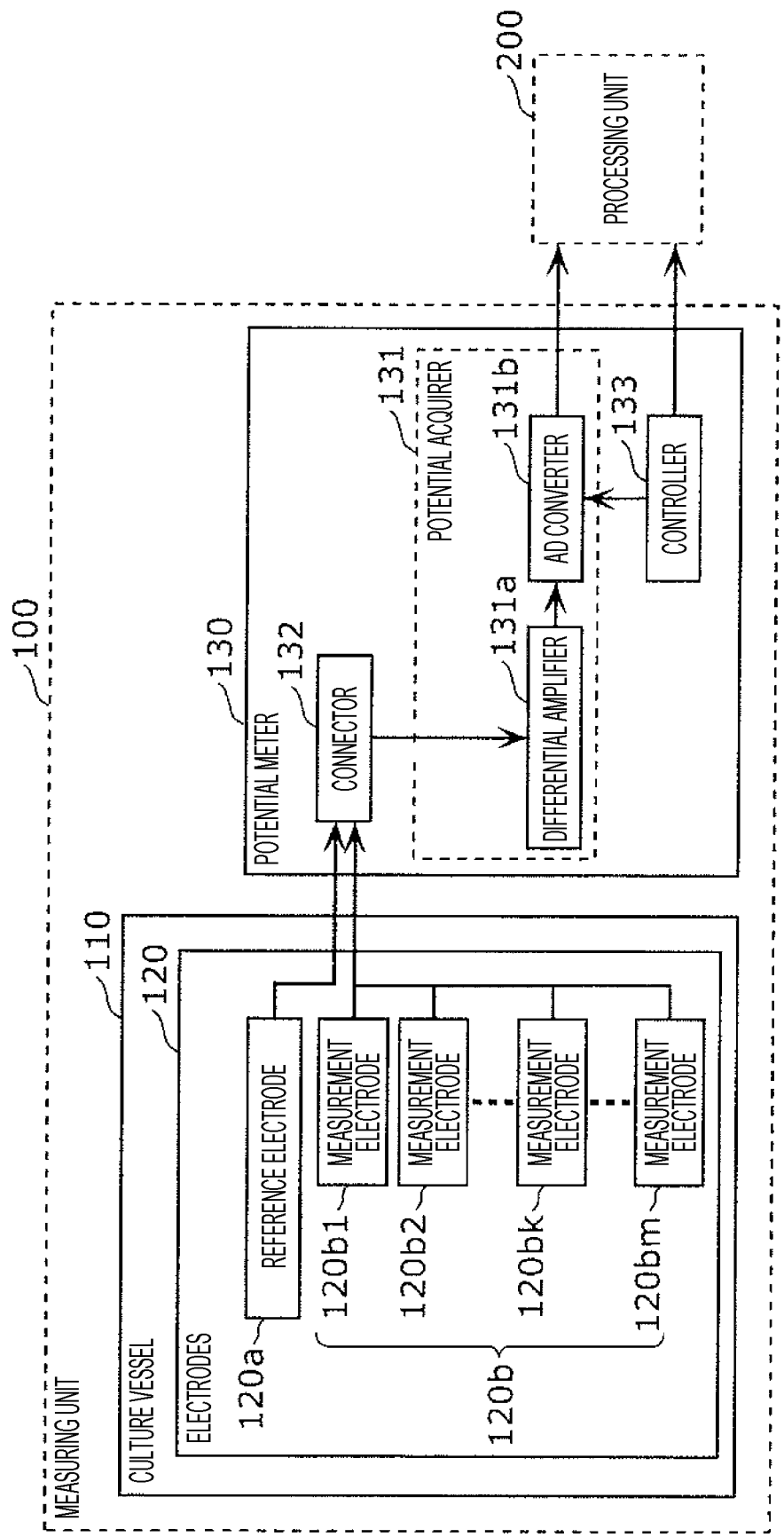
FIG. 9 is a block diagram illustrating an example of the hardware configuration of a potential acquirer in FIG. 1.

The configuration and operation of the potential meter 130 of the measuring unit 100 will be described. FIG. 9 is a block diagram illustrating an example of the hardware configuration of the potential acquirer 131 in FIG. 1. In the example illustrated in FIG. 9, the potential acquirer 131 is composed of a differential amplifier 131*a* and an analog-to-digital (AD) converter 131*b*.

The differential amplifier 131*a* outputs the potential of each of the measurement electrodes 120*b*1 to 120*bm* as the difference from the reference potential of the reference electrode 120*a* by using the potential of the reference electrode 120*a* as the reference potential.

The AD converter 131*b* converts an analog signal into a digital signal. The AD converter 131*b* converts the potential, which is input thereto as an analog signal at predetermined time intervals, into a numeric value. The predetermined time interval is, for example, an interval corresponding to 20000 times per second, 0.5 milliseconds, or the like. The AD converter 131*b* converts a potential into a numerical value in synchronism between the measurement electrodes 120*b*1 to 120*bm*. That is, the AD converter 131*b* converts potentials that are measured at the measurement electrodes 120*b*1 to 120*bm* at the same time into numerical values.

Figure 10:
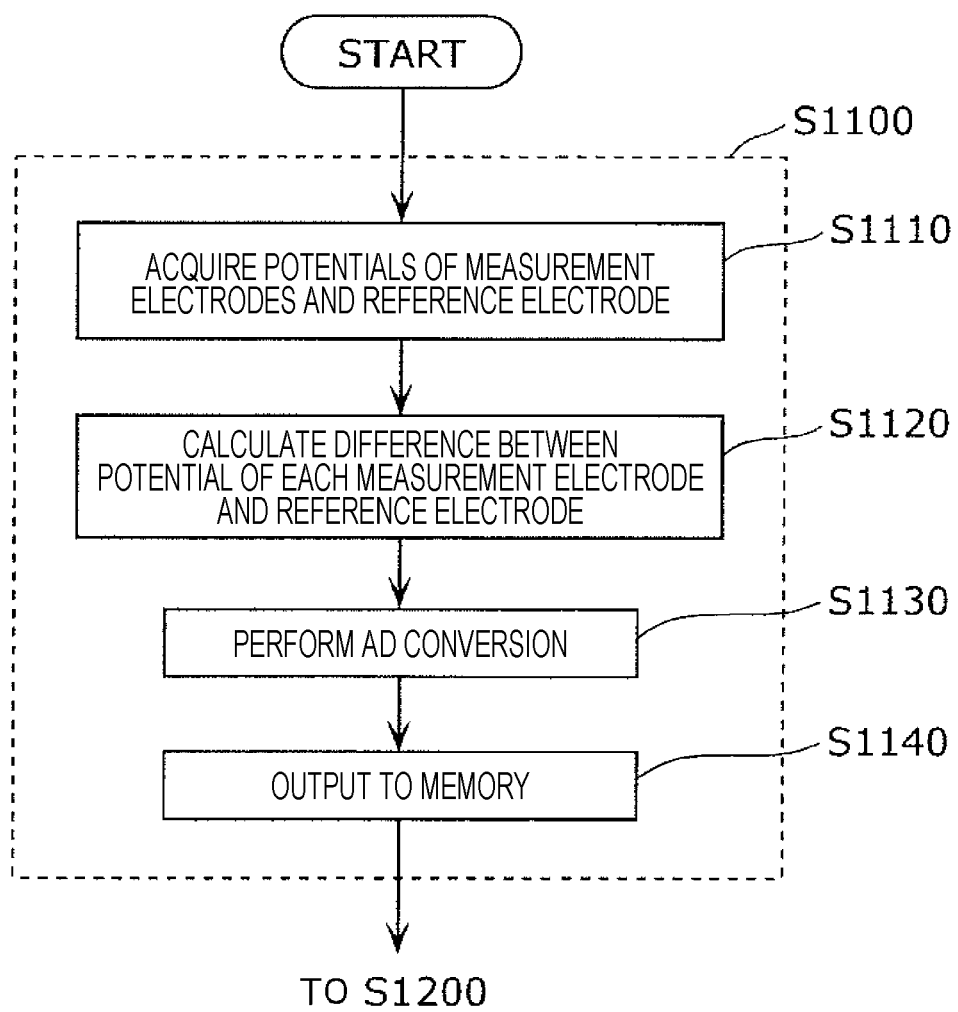
FIG. 10 is a flowchart illustrating an example of the details of step S1100 in FIG. 8.

Referring to FIG. 10, an operation of the potential meter 130, including the potential acquirer 131 configured as described above, will be described. FIG. 10 is a flowchart illustrating an example of the operation of the potential meter 130 of the electric reaction measuring apparatus 1 according to the first embodiment. FIG. 10 is also a flowchart illustrating an example of the details of step S1100 in FIG. 8.

(Step S1110) First, the differential amplifier 131*a* simultaneously acquires the potentials of the measurement electrodes 120*b*1 to 120*bm* and the potential of the reference electrode 120*a*.

(Step S1120) Next, the differential amplifier 131a obtains the potential difference between each of the measurement electrodes 120b1 to 120bm and the reference electrode 120a. That is, the differential amplifier 131a obtains the potential difference between the measurement electrode 120bk (k=1 to m) and the reference electrode 120a. The operation of the differential amplifier 131a is also called "differential amplification". As described above, signals output from the measurement electrodes 120b1 to 120bm to the differential amplifier 131a are independent from each other due to the insulation function of the partition member 140 and the like.

(Step S1130) Next, the AD converter 131b acquires the potential difference between each of the measurement electrodes 120b1 to 120bm and the reference electrode 120a, which has been obtained by the differential amplifier 131a in step S1120, at predetermined time intervals and converts the potential difference into a numeric value. The time interval may be determined by the controller 133. Moreover, the controller 133 may perform synchronization of the time interval or the time at which the potential is to be obtained, between the measurement electrodes 120b1 to 120bm.

(Step S1140) Next, the AD converter 131b outputs the potential difference of each of the measurement electrodes 120b1 to 120bm, which has been converted into a numeric value in step S1130, to the memory 210 together with information about the time interval or the time when the potential was converted into a numeric value. The time interval or the time when the potential was converted into a numeric value may be regarded as the measurement interval or the measurement time of the potential.

1-4. Advantageous Effects

As described above, in the electric reaction measuring apparatus 1 according to the first embodiment, the measurement electrodes 120b1 to 120bm are separated from each other in the culture vessel 110 by the partition wall 140a of the partition member 140. When one cell or tissue is in contact with or in proximity to each measurement electrode 120bk (k=1 to m), the electric reaction measuring apparatus 1 performs principal component analysis on potential waveforms simultaneously measured at the measurement electrodes 120b1 to 120bm. Moreover, the electric reaction measuring apparatus 1 regards a potential waveform that is extracted from principal components for each measurement electrode 120b1 to 120bm as a noise common to the measurement electrodes, and subtracts the potential waveform of noise from the potential waveform measured at each of the measurement electrodes 120b1 to 120bm. Accordingly, the electric reaction measuring apparatus 1 can measure an electric reaction that reflects the activity of a cell or tissue disposed at each of the measurement electrodes 120b1 to 120bm independently for the cell or tissue and with high accuracy. Thus, it is possible to measure an electrical reaction due to the specific activity of a cell or tissue with higher accuracy, because noise from the outside of the cell or tissue, which influences measurement signals of the measurement electrodes 120b1 to 120bm, is removed. Thus, a user can easily determine whether the activity of a cell or tissue is good, from the output result of the electric reaction measuring apparatus 1 using the electrical reaction. When the electric reaction measuring apparatus 1 is applied to a technology for automatically determining, by machine learning, whether an activity of a cell or tissue is good based on an electric reaction of the cell or tissue, machine learning of an automatic determination process is facilitated, and it is possible to increase the determination accuracy. Also when the electric reaction measuring apparatus 1 is applied to a determination method that does not use machine learning, it is easy to define determination criteria, and it is possible to increase the determination accuracy. The electric reaction measuring apparatus 1 facilitates, for example, selection of cells or tissues for regenerative medicine by making it easier to determine whether an activity of a cell or tissue is good and by increasing the determination accuracy.

First Modification of First Embodiment

An electrode 120 of an electric reaction measuring apparatus 1 according to a first modification of the first embodiment will be described. In the first embodiment, the electrode 120 disposed in the culture vessel 110 includes one reference electrode 120a and one or more measurement electrodes 120b. In the present modification, the electrode 120 includes multiple reference electrodes and one or more measurement electrodes. In the present modification, reference electrodes 120a1 to 120a4 are connected to a common circuit, that is, are common to each other on a circuit. As in the first embodiment, measurement electrodes 120b are respectively connected to circuits that are independent from each other.

Figure 11A:
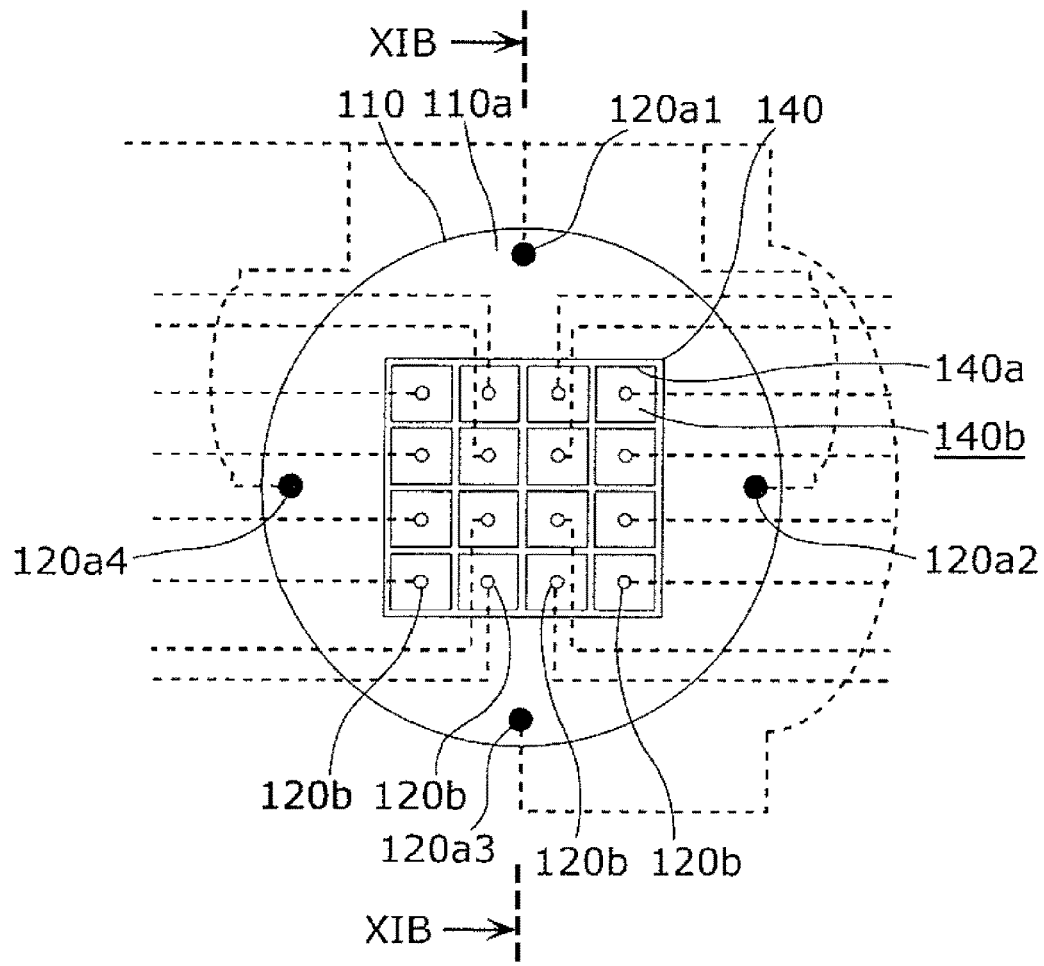
FIG. 11A is a schematic plan view, similar to FIG. 4A, illustrating electrodes of an electric reaction measuring apparatus according to a first modification of the first embodiment.
Figure 11B:
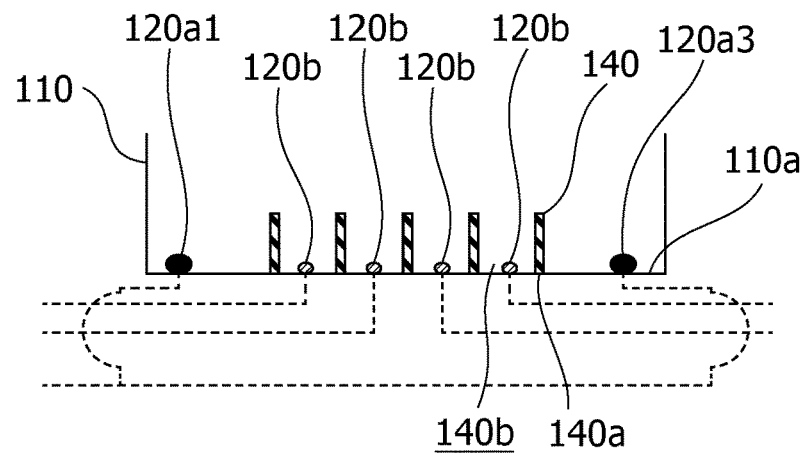
FIG. 11B is a schematic sectional side view taken along line XIB-XIB in FIG. 11A.

Referring to FIGS. 11A and 11B, the configuration of the reference electrodes 120a1 to 120a4 and the measurement electrodes 120b according to the first modification will be described. FIG. 11A is a schematic plan view, similar to FIG. 4A, illustrating electrodes of the electric reaction measuring apparatus according to the first modification of the first embodiment. FIG. 11B is a schematic sectional side view taken along line XIB-XIB in FIG. 11A. In FIGS. 11A and 11B, wires of circuits connected to the reference electrodes 120a1 to 120a4 and the measurement electrodes 120b are schematically shown by broken lines.

Also in the first modification of the first embodiment, difference in the liquid surface of a culture solution, as illustrated in FIGS. 4C and 4D, is taken into consideration. When the height of the liquid surface of the culture solution is held at a height exceeding the height of the partition wall 140a, the measurement electrodes 120b and the reference electrodes 120a are electrically connected to each other through the culture solution. However, as in FIG. 4C of the first embodiment, electrical separation by the partition wall 140a is sufficiently large. As illustrated in FIGS. 11A and 11B, in the first modification of the first embodiment, the reference electrodes 120a are connected as an electric circuit and electrically common to each other. When the liquid surface of culture solution is held at a height that does not exceed the height of the partition wall 140a, the measurement electrodes 120b are not electrically connected to each other via the culture solution and electrical separation is sufficiently large. Moreover, the measurement electrodes 120b and the reference electrodes 120a are not electrically connected to each other via the culture solution and electrical separation is sufficiently large. In the examples illustrated in FIGS. 11A and 11B, the reference electrodes 120a are electrically connected to each other via the culture solution. The reference electrodes 120a are electrically connected to each other not only via the culture solution but also connected through an electric circuit and electrically common to each other.

As illustrated in FIGS. 11A and 11B, in the culture vessel 110, the reference electrodes 120a1, 120a2, 120a3, and 120a4, which are electrically common to each other on the circuit, and the measurement electrodes 120b, which are respectively connected to different circuits, are disposed. In the example illustrated in FIG. 11A, four reference electrodes 120a1 to 120a4 are disposed around the partition member 140 at regular intervals so as to surround the partition member 140, that is, all wells 140b. As in the first embodiment, the reference electrodes 120a1 to 120a4 are disposed on the bottom wall 110a of the culture vessel 110. Thus, the distance from each well 140b of the partition member 140 to one of the reference electrodes 120a1 to 120a4 that is nearest to the well 140b is smaller than that in the first embodiment. That is, variation in the distances is small between the wells 140b. Regarding the sum and the average of the distances from each well 140b to the four reference electrode 120a1 to 120a4, variations in the sum and the average are small between the wells 140b. Thus, between the wells 140b, variation in the distances from the wells 140b to the reference electrodes 120a1 to 120a4 is small. The configuration of each measurement electrode 120b is similar to that in the first embodiment.

As shown by broken lines in FIG. 11A, the circuits of the reference electrodes 120a1 to 120a4 are common to each other. Thus, although the potentials at the reference electrodes 120a1 to 120a4 are different, because the circuits connected thereto are common to each other, the potentials of the reference electrodes 120a1 to 120a4 are common to each other, that is, the reference potentials of the reference electrodes 120a1 to 120a4 are common to each other. The reference electrodes 120a1 to 120a4 are connected to the connector 132 of the potential meter 130 via one wire, and the potentials of the reference electrodes 120a1 to 120a4 are collectively acquired by the potential acquirer 131 as one potential. Thus, the potential differences between the measurement electrodes 120b and the reference electrodes 120a1 to 120a4 acquired by the potential acquirer 131 represent values obtained by, for example, averaging the potential differences between the measurement electrodes 120b and the reference electrodes 120a1 to 120a4, and represent values in which an influence due to the positional relationship between the reference electrodes 120a1 to 120a4 and the measurement electrodes 120b is suppressed.

As described above, with the electric reaction measuring apparatus 1 according to the first modification of the first embodiment, the reference electrodes 120a1 to 120a4 in the culture vessel 110 are disposed at regular intervals so as to surround all wells 140b, and, further, the circuits of the reference electrodes 120a1 to 120a4 are electrically common to each other. Thus, for the measurement electrodes 120b, variation in the distances between the measurement electrodes 120b and the reference electrodes 120a1 to 120a4 is reduced. Then, it is possible to reduce the change in phase of noise that commonly influences the measurement electrodes 120b in accordance with the distances between the measurement electrodes 120b and the reference electrodes 120a1 to 120a4, and the noise is prevented from becoming difficult to be extracted as a principal component. That is, by disposing the reference electrodes 120a1 to 120a4 so as to surround all wells 140b, for example, at regular intervals, it is possible to remove noise with higher accuracy by performing principal component analysis. With the configuration of the electrodes in the first modification, it is possible to measure an electrical reaction of a cell or tissue disposed at each of the measurement electrodes 120b, which reflects an activity of the cell or tissue, independently for the cell or tissue and with higher accuracy. It becomes easy for a user to determine or to automatically determine whether the activity of a cell or tissue is good, because an electric reaction due to a specific activity of the cell or tissue is measured with higher accuracy. Second Modification of First Embodiment An electrode 120 of an electric reaction measuring apparatus 1 according a second modification of the first embodiment will be described. In the present modification, the configuration of the reference electrode differs from those in the first embodiment and the first modification. To be specific, the reference electrode is disposed on the partition wall 140a of the well 140b.

Figure 12A:
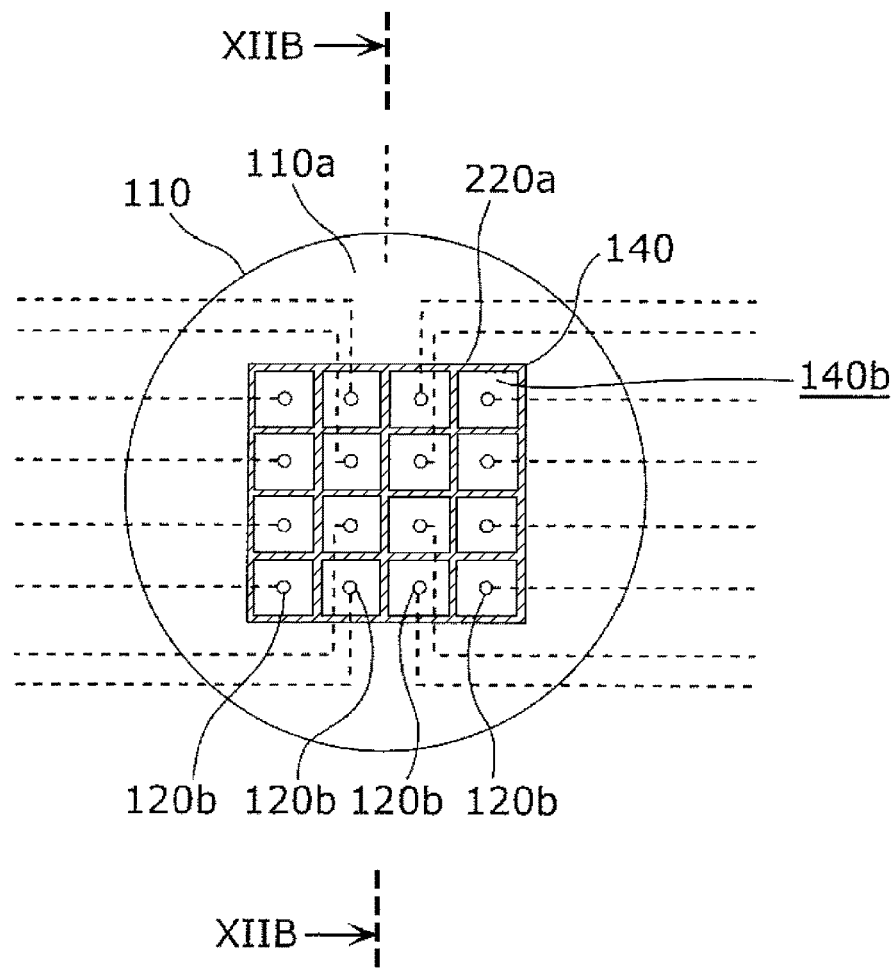
FIG. 12A is a schematic plan view, similar to FIG. 4A, illustrating electrodes of an electric reaction measuring apparatus according to a second modification of the first embodiment.
Figure 12B:
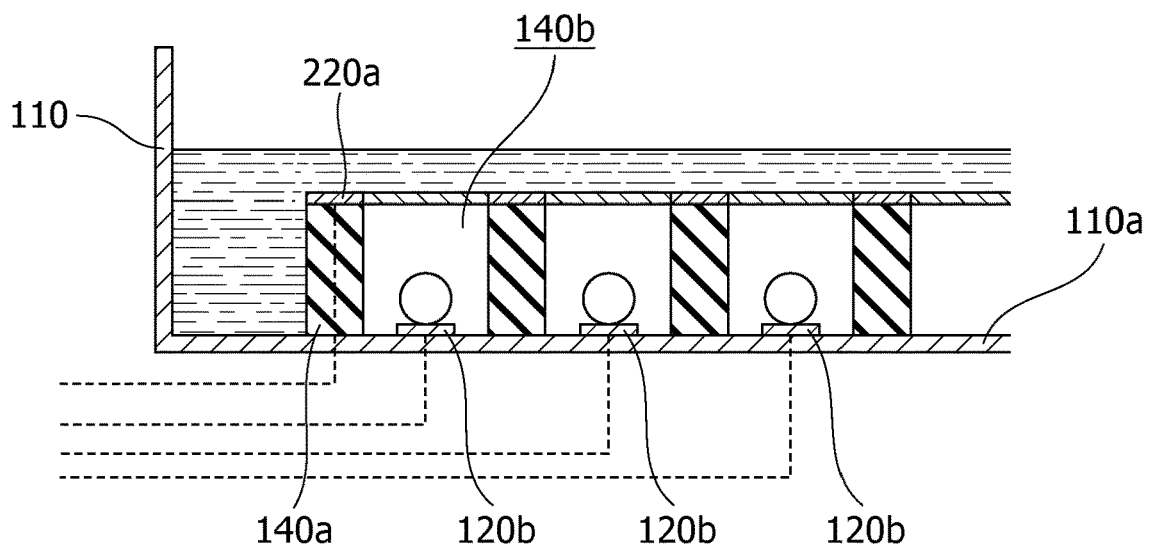
FIG. 12B is a schematic sectional side view taken along line XIIB-XIIB in FIG. 12A.

Referring to FIGS. 12A and 12B, the configuration of a reference electrode 220a and measurement electrodes 120b according to the second modification will be described. FIG. 12A is a schematic plan view, similar to FIG. 4A, illustrating the electrodes of the electric reaction measuring apparatus 1 according to the second modification of the first embodiment. FIG. 12B is a schematic sectional side view taken along line XIIB-XIIB in FIG. 12A. In FIGS. 12A and 12B, wires of circuits connected to the reference electrode 220a and the measurement electrodes 120b are schematically shown by broken lines.

As illustrated in FIGS. 12A and 12B, in the culture vessel 110, one reference electrode 220a is disposed on the partition wall 140a of the partition member 140, and the measurement electrodes 120b, which are similar to those in the first embodiment, are disposed inside of the partition wall 140a. In the example illustrated in FIG. 12A, the reference electrode 220a is disposed on an upper part of the partition wall 140a opposite from the bottom wall 110a of the culture vessel 110. To be specific, the reference electrode 220a is disposed on the entirety of the upper part of the partition wall 140a, and has a mesh-like shape, to be specific, a lattice-like shape similar to the shape of the partition wall 140a. The reference electrode 220a is disposed so as to surround each measurement electrodes 120b and each well 140b when seen from above. Therefore, the distance between the reference electrode 220a and the measurement electrodes 120b is considerably reduced from that in the first embodiment and the first modification, and, between the measurement electrodes 120b, there is substantially no difference in the distance. In FIG. 12A, the reference electrode 220a is disposed on the entirety of the upper part of the partition wall 140a. Alternatively, the reference electrode 220a may be partially disposed on crossing parts of the partition wall 140a or the like. Further alternatively, the reference electrode 220a may be disposed between the partition wall 140a and the bottom wall 110a of the culture vessel 110. The reference electrode 220a is connected to one circuit and allows circuits connected thereto to be common to each other.

The reference electrode 220a is disposed on the upper part of the partition wall 140a around the wells 140b and are not in contact with tissues or cells in the wells 140b. When the height of the liquid surface of culture solution is greater than the height of the partition wall 140a, the reference electrode 220a is in contact with the culture solution. Therefore, when measuring the potential by using the reference electrode 220a and the measurement electrodes 120b, the culture vessel 110 is filled with the culture solution so that the height of the liquid surface of the culture solution is greater than or equal to the height of the partition wall 140a.

With the configuration of the reference electrode 220a described above, for all measurement electrodes 120b, the distances between the measurement electrodes 120b and the reference electrode 220a are substantially the same. The reference electrode 220a is connected to the connector 132 of the potential meter 130 via one wire, and the potential of the reference electrode 220a is acquired by the potential acquirer 131 as a reference potential.

In the second modification of the first embodiment, the reference electrode 220a is on the upper part of the partition wall 140a as illustrated in FIGS. 12A and 12B, and the liquid surface of the culture solution is held at a height exceeding the height of the partition wall 140a. Accordingly, the measurement electrodes 120b and the reference electrode 120a are electrical connected to each other through the culture solution. However, as with FIG. 4C in the first embodiment, electrical separation between the measurement electrodes 120b due to the partition wall 140a is sufficiently large.

As described above, with the electric reaction measuring apparatus 1 according to the second modification of the first embodiment, one reference electrode 220a in the culture vessel 110 is disposed on the upper part of the partition wall 140a of the wells 140b. Thus, for the measurement electrodes 120b, variation in the distances between the measurement electrodes 120b and the reference electrode 220a is reduced to the minimum. Then, it is possible to suppress noise that commonly influences the measurement electrodes 120b from becoming difficult to be extracted as a principal component due to the distances between the measurement electrodes 120b and the reference electrode 220a. That is, by disposing the mesh-shaped reference electrode 220a so as to surround each well 140b, it is possible to remove noise with higher accuracy by performing principal component analysis. With the configuration of the electrodes in the second modification, it is possible to measure an electrical reaction of a cell or tissue disposed at each of the measurement electrodes 120b, which reflects an activity of the cell or tissue, independently for the cell or tissue and with higher accuracy. It becomes easy for a user to determine or to automatically determine whether the activity of a cell or tissue is good, because an electric reaction due to a specific activity of the cell or tissue is measured with higher accuracy.

Second Embodiment

An electric reaction measuring apparatus according to a second embodiment will be described. The electric reaction measuring apparatus according to the second embodiment differs from the first embodiment in the configuration of a signal processor 220A of a processing unit 200A. Hereafter, the difference between the second embodiment and the first embodiment will be mainly described.

In the first embodiment, the signal processor 220 of the processing unit 200 extracts a component common to the multiple measurement electrodes 120b as noise by performing principal component analysis. In the second embodiment, the signal processor 220A of the processing unit 200A determines, by using a correlation function, the similarity between the synthesized waveforms of principal components extracted by performing principal component analysis, groups similar synthesized waveforms as the same noise only with shifted phases, and removes the noise. Thus, it is possible to collectively remove, based on the similarity of waveforms, noise that may be extracted as a principal component whose contribution ratio to variance is small and may remain without being removed due to phase differences between the potentials of the measurement electrodes 120b.

2-1. Configuration of Signal Processor of Electric Reaction Measuring Apparatus

Figure 13:
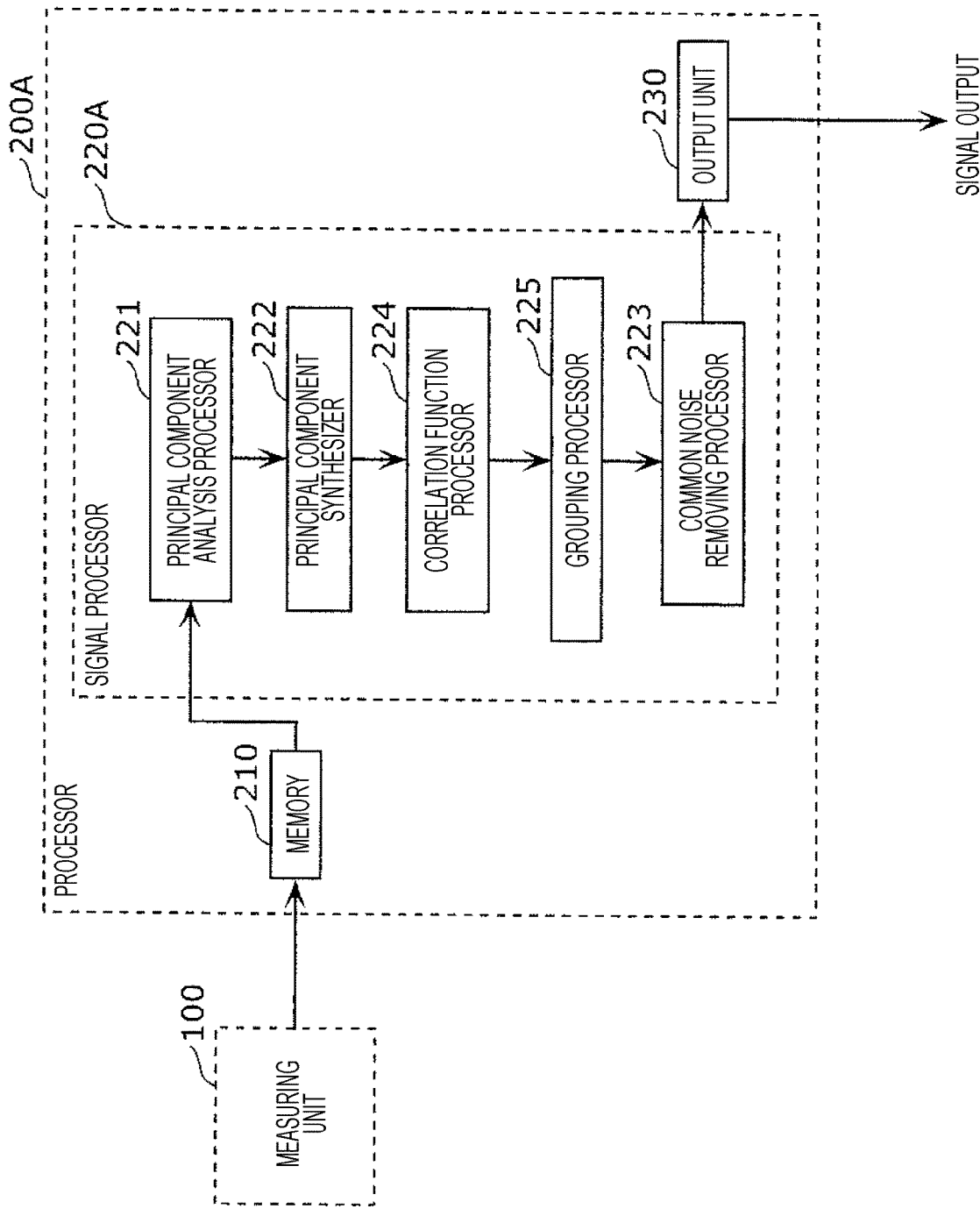
FIG. 13 is a block diagram illustrating an example of the functional configuration of a signal processor of an electric reaction measuring apparatus according to a second embodiment.

The configuration of the signal processor 220A of the processing unit 200A of the electric reaction measuring apparatus according to the second embodiment will be described. FIG. 13 is a block diagram illustrating an example of the functional configuration of the signal processor 220A of the electric reaction measuring apparatus according to the second embodiment. As illustrated in FIG. 13, the processing unit 200A includes the memory 210, the signal processor 220A, and the output unit 230. The signal processor 220A includes the principal component analyzer 221, the principal component synthesizer 222, a correlation function processor 224, a grouping processor 225, and the common noise remover 223. The configurations of the principal component analyzer 221 and the principal component synthesizer 222 are the same as those in the first embodiment.

The correlation function processor 224 obtains a correlation coefficient by applying, to a first synthesized waveform, which is the synthesized waveform of potential waveforms due to respective principal components of the measurement electrodes 120b1 to 120bm synthesized by the principal component synthesizer 222, a correlation function for the first synthesized waveform of two different principal components between two measurement electrodes. For example, a correlation coefficient is obtained between a first synthesized waveform Yik due to the i-th principal component of the measurement electrode 120bk and a first synthesized waveform Yjk+1 due to the j-th principal component of the measurement electrode 120bk+1. That is, regarding a first synthesized waveform as a potential corresponding to a principal component, the correlation function processor 224 calculates a correlation coefficient of first synthesized waveforms corresponding to two principal components.

When the absolute value of the correlation coefficient of different principal components between the measurement electrodes 120b1 to 120bm, which has been calculated by the correlation function processor 224, is greater than or equal to a predetermined threshold value, the grouping processor 225 determines that the two principal components are the same principal component with only shifted phases, and performs grouping so that the two principal components are included in one group. That is, the grouping processor 225 groups the two principal components whose correlation coefficient is greater than or equal to a predetermined value into one group.

The grouping processor 225 calculates, for each group of principal components that have been grouped, the sum of the contribution ratios, to the total variance, of all principal components included in the group, and regards the sum as the contribution ratio of the group. That is, the grouping processor 225 calculates, as the contribution ratio of the group, the sum of the contribution ratios of all principal components included in the group.

The grouping processor 225 sorts the groups in descending order of contribution ratio, selects a predetermined number of groups in descending order or selects groups for which the contribution ratios thereof accumulated in descending order exceeds a predetermined value, and determines all of the principal components included in the selected groups as noise to be removed. That is, the grouping processor 225 extracts, in descending order of contribution ratio, the groups and the principal components that are not included in the groups, and estimates that the sum of potentials corresponding to principal components that are included in the extracted groups and the extracted principal components that are not included in the groups is noise.

Regarding the principal components determined by the grouping processor 225, the common noise remover 223 removes noise, for all measurement electrodes 120b1 to 120*bm*, by subtracting a potential waveform that is a first synthesized waveform synthesized for each principal component from the measured potential waveform; and outputs the potential waveform after noise removal to the output unit 230. That is, for the potential waveform measured at each measurement electrode 120*bk* (k=1 to m), the common noise remover 223 subtracts the sum of the first synthesized waveforms Yik corresponding to the measurement electrode 120*bk* and corresponding to the respective principal components determined by the grouping processor 225 from a potential waveform measured at the measurement electrode 120*bk*, that is, the potential.

2-2. Operation of Electric Reaction Measuring Apparatus

Figure 14:
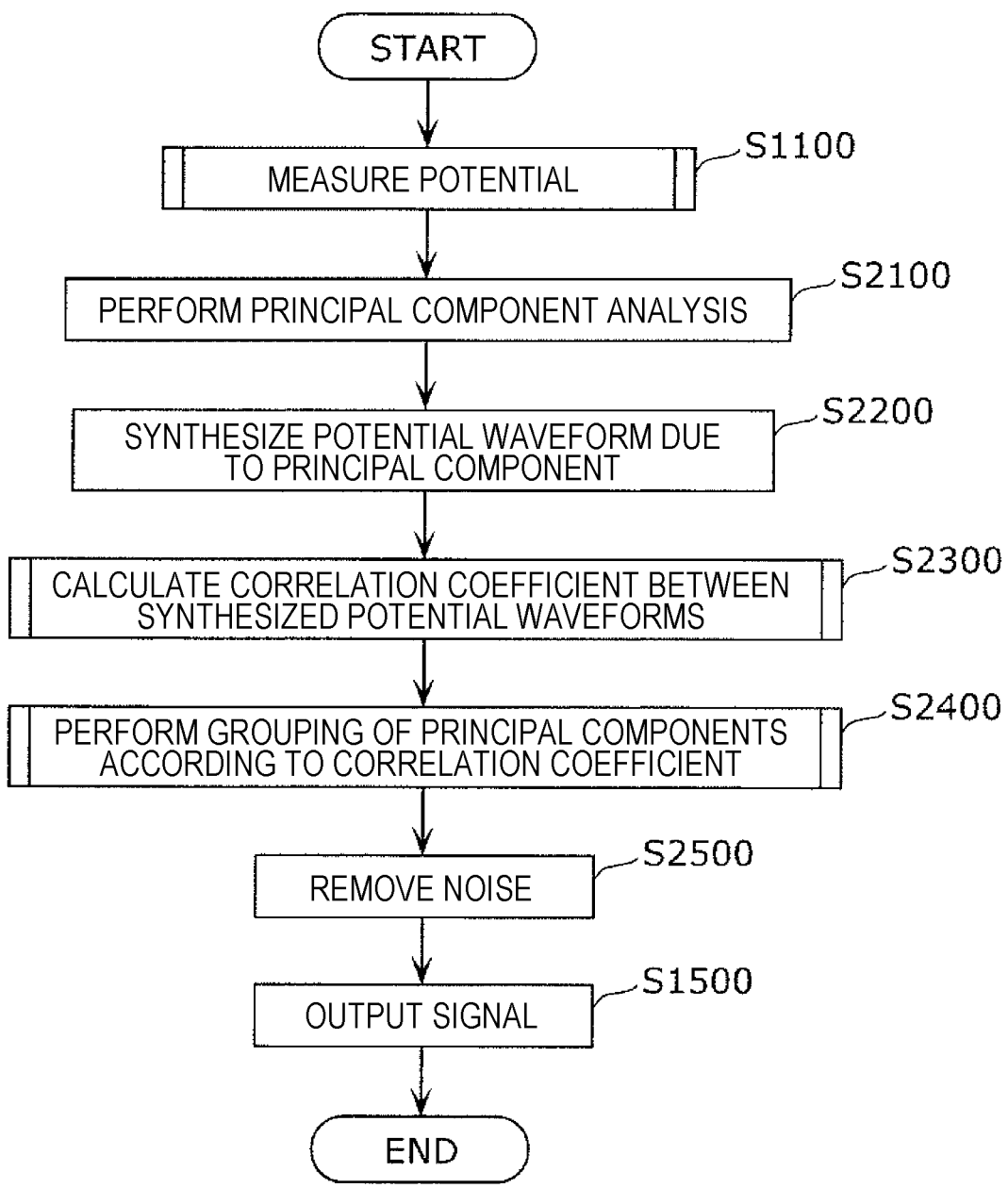
FIG. 14 is a flowchart illustrating an example of an operation performed by the electric reaction measuring apparatus according to the second embodiment.

Referring to FIG. 14, an operation of the electric reaction measuring apparatus according to the second embodiment, which includes the signal processor 220A configured as described above, will be described. FIG. 14 is a flowchart illustrating an example of the operation performed by the electric reaction measuring apparatus according to the second embodiment.

(Step S1100) The principal component analyzer 221 performs step S1100 in the same way as step S1100 in the first embodiment.

(Step S2100) The principal component analyzer 221 performs step S2100 in the same way as step S1200 in the first embodiment.

(Step S2200) The principal component synthesizer 222 performs step S2200 in the same way as step S1300 in the first embodiment.

(Step S2300) The correlation function processor 224 obtains, for a first synthesized waveform that is the potential waveform of each principal component of each of the measurement electrodes 120*b*1 to 120*bm* synthesized by the principal component synthesizer 222 in step S2200, the correlation coefficient, for the first synthesized waveform that is a potential waveform of two different principal components, between two measurement electrodes. FIGS. 15A and 15B each show an example of the correlation coefficient obtained in step S2300. FIGS. 15A and 15B each show an example of some of calculation results obtained by the correlation function processor 224 of the electric reaction measuring apparatus according to the second embodiment. Details of step S2300 will be described below.

(Step S2400) the grouping processor 225 extracts combinations of principal components for which the absolute value of the correlation coefficient of different principal components between two measurement electrodes, which has been calculated by the correlation function processor 224 in step S2300, is greater than or equal to a predetermined threshold value; and performs grouping so that these principal components are included in one group. The grouping processor 225 calculates, for each group, the sum of the contribution ratios of principal components included in the group to the total variance, and regards the sum as the contribution ratio of the group. The grouping processor 225 sorts the groups in descending order of contribution ratio, selects a predetermined number of groups in descending order or selects groups for which contribution ratios thereof accumulated in descending order exceeds a predetermined value, and determines the principal components included in the selected groups as noise to be removed. Details of the operation in step S2400 will be described below.

(Step S2500) Regarding the principal components determined in step S2400 as noise to be removed, the common noise remover 223 obtains a remainder by subtracting a noise waveform that is a first synthesized waveform corresponding to the principal component of each of the measurement electrodes 120*b*1 to 120*bm* synthesized in step S2300 from the potential waveform that is a measured value at each of the measurement electrodes 120*b*1 to 120*bm*. The common noise remover 223 regards a time waveform of the remainder, which is obtained by subtracting the first synthesized waveform for all principal components determined in step S2400, as a potential waveform at each of the measurement electrodes 120*b*1 to 120*bm* after noise removal; and outputs the potential waveform to the output unit 230.

(Step S1500) The output unit 230 outputs the potential waveform after noise removal of each of the measurement electrodes 120*b*1 to 120*bm*, which has been calculated by the common noise remover 223 in step S1400, as a numeric series in which a potential is paired with a time when the potential is measured.

2-3. Details of Step S2300

Figure 16:
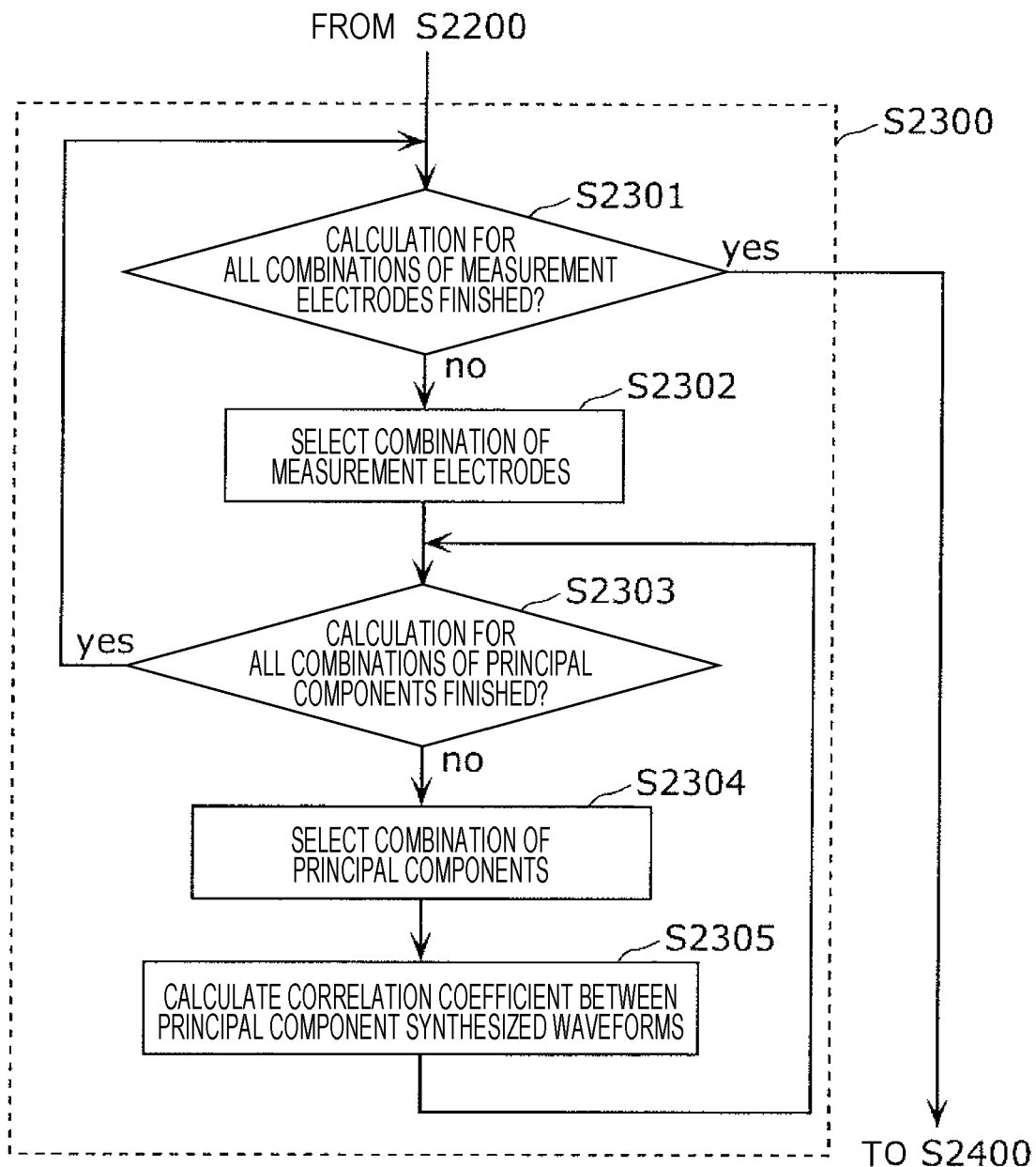
FIG. 16 is a flowchart illustrating an example of the details of step S2300 in FIG. 14.

Referring to FIG. 16, the details of the operation of the correlation function processor 224 in step S2300 will be described. FIG. 16 is a flowchart illustrating an example of the details of step S2300 in FIG. 14.

(Step S2301) The correlation function processor 224 determines, for all combinations of pairs of measurement electrodes extracted from the measurement electrodes 120*b*1 to 120*bm*, whether calculation of the correlation coefficient of the first synthesized waveforms of principal components of all combinations of measurement electrodes has finished. The correlation function processor 224 proceeds to step S2400 if the calculation has finished ("yes" in step S2301). The correlation function processor 224 proceeds to step S2302 if the calculation has not finished ("no" in step S2301).

(Step S2302) The correlation function processor 224 selects one combination from the combinations of measurement electrodes for which the correlation coefficient between principal components has not been calculated.

(Step S2303) The correlation function processor 224 determines whether calculation of the correlation coefficient has finished for all combinations of different principal components, between the principal components of two measurement electrodes selected in step S2302. If the calculation has finished ("yes" in step S2303), the correlation function processor 224 returns to step S2301. If the calculation has not finished ("no" in step S2303), the correlation function processor 224 proceeds to step S2304.

(Step S2304) The correlation function processor 224 selects one combination from the combinations of principal components whose correlation coefficient has not been calculated.

(Step S2305) The correlation function processor 224 calculates, for the combinations of principal components selected in step S2304, the correlation coefficient between the first synthesized waveforms of two principal components.

The correlation function processor 224 can obtain the correlation coefficients of the first synthesized waveforms of potentials in all combinations of different principal components for principal components of two measurement electrodes, by repeating steps S2303 to S2305.

FIGS. 15A and 15B each show an example of the results of calculating the correlation coefficients. FIG. 15A is a table showing an example of the correlation coefficients between principal components in the combination of the measurement electrode 120*bk* and the measurement electrode 120*bk*+1. FIG. 15B is a table showing an example of the correlation coefficients between principal components in the combination of the measurement electrode 120*bk*+2 and the measurement electrode 120*bk*+3. The correlation function processor 224 does not calculate the correlation coefficient between the same principal components of different measurement electrodes, and calculates the correlation coefficient between different principal components of different measurement electrodes.

The correlation function processor 224 can obtain correlation coefficients as shown in FIGS. 15A and 15B for all combinations of measurement electrodes and all combinations of principal components, by repeating steps S2301 to S2305.

2-4. Details of Step S2400

Figure 17:
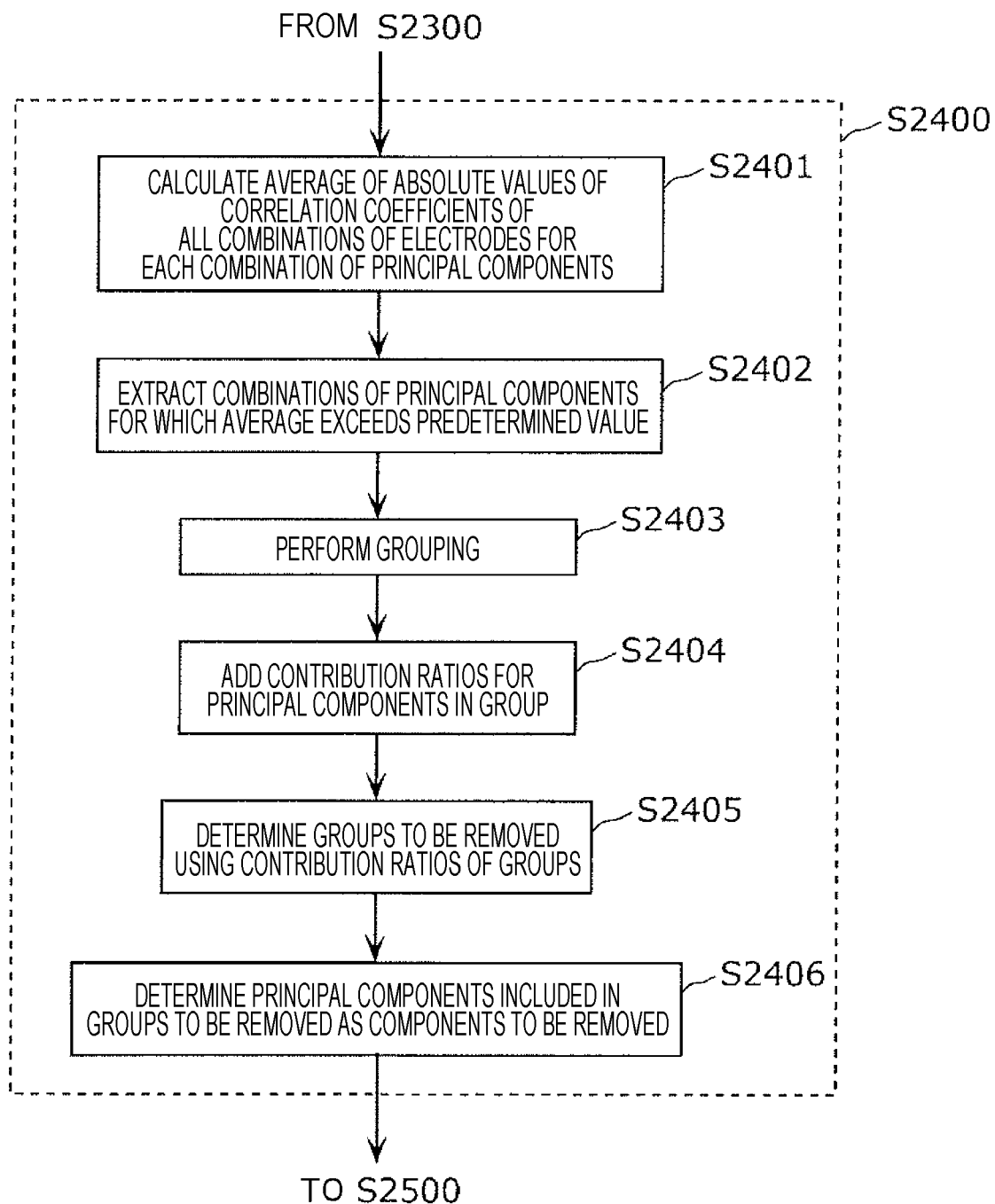
FIG. 17 is a flowchart illustrating an example of the details of step S2400 in FIG. 14.

Referring to FIG. 17, the detailed operation of the grouping processor 225 in step S2400 will be described. FIG. 17 is a flowchart illustrating an example of the details of step S2400 in FIG. 14.

(Step S2401) The grouping processor 225 calculates, for each combination of the measurement electrodes 120*b*1 to 120*bm*, the absolute value of the correlation coefficient of each combination of principal components, and calculates the average of the absolute values of the correlation coefficients for each combination of principal components regarding all combinations of principal components included in the combination of the measurement electrodes. For example, in the examples shown in FIGS. 15A and 15B, for the combination of the first principal component and the second principal component, the grouping processor 225 obtains the average of the absolute values of all correlation coefficients, which are calculated between the first principal component and the second principal component as follows: the absolute value of the correlation coefficient between the first principal component of the measurement electrode 120*bk* and the second principal component of the measurement electrode 120*bk*+1; the absolute value of the correlation coefficient between the second principal component of the measurement electrode 120*bk* and the first principal component of the measurement electrode 120*bk*+1; the absolute value of the correlation coefficient between the first principal component of the measurement electrode 120*bk*+2 and the second principal component of the measurement electrode 120*bk*+3; and the absolute value of the correlation coefficient between the second principal component of the measurement electrode 120*bk*+2 and the first principal component of the measurement electrode 120*bk*+3. FIG. 18 illustrates an example of results of calculating the average of the absolute values of the correlation coefficients for each combination of principal components in the examples shown in FIGS. 15A and 15B. The absolute value of a correlation coefficient has a value in the range of 0 to 1, and a value closer to 1 indicates a closer similarity between two principal components.

(Step S2402) The grouping processor 225 extracts, from the combinations of principal components, combinations of principal components for which the average of the absolute values of the correlation coefficients obtained in step S2401 exceeds a predetermined value. The predetermined value is, for example, 0.7. In the example illustrated FIG. 18, the combination of the first principal component and the third principal component and the combination of the third principal component and the fourth principal component satisfy this criterion.

(Step S2403) The grouping processor 225 groups the combinations of principal components extracted in step S2402, that is, performs grouping. At this time, first, the grouping processor 225 groups two extracted combinations into one group. Moreover, when the two extracted combinations have overlap in included principal components as in the example shown in FIG. 18, the grouping processor 225 groups the combinations including overlapping principal components into one group. That is, in the example shown in FIG. 18, the grouping processor 225 determines, in the first principal component and the third principal component, and in the third principal component and the fourth principal component, the third principal component as the overlapping principal component; and groups the first principal component, the third principal component, and the fourth principal component into one group. Thus, a set of principal components that have overlap with any of the principal components are grouped into one group, and a set of principal components that do not have overlap with any of the principal components is grouped into another group. Principal components that are not included in any of the groups are treated as ungrouped principal components.

(Step S2404) The grouping processor 225 calculates, for a group of principal components including two or more principal components, contribution ratios to the variance of the entire data of principal components included in the group, and determines the sum of the contribution ratios of the principal components of each group as the contribution ratio of the group. Moreover, the grouping processor 225 groups principal components that have not been grouped in step S2403 into one group, and calculates the contribution ratio of the group in the same way as described above. The contribution ratio of a group composed of one principal component is the contribution ratio of the principal component.

(Step S2405) The grouping processor 225 synthesizes the contribution ratios of groups grouped in step S2403 and the contribution ratios of principal components that have not been grouped in step S2403, and extracts a predetermined number of groups in descending order of contribution ratio. Alternatively, the grouping processor 225 extracts, in descending order of contribution ratio, groups for which the sum of contribution ratios thereof exceeds a predetermined contribution ratio. In this way, each of principal components that have not been grouped is also treated as one group, and extraction of groups is performed by using the contribution ratios of all groups. Groups extracted as describe above include groups that have been grouped in step S2403 and include two or more principal components and groups that have not been grouped in step S2403 and include one principal component.

(Step S2406) The grouping processor 225 determines all principal components included in groups extracted in step S2405 as components to be removed as noise.

2-5. Advantageous Effects

As described above, the electric reaction measuring apparatus according to the second embodiment obtains the correlation coefficient of synthesized waveforms of principal components and groups the principal components according to the similarity of the synthesized waveforms based on the correlation coefficients. That is, the electric reaction measuring apparatus groups principal components that are the same but that may be extracted as different principal components as the phase of noise shifts due to the positions of the measurement electrodes, the distances between the measurement electrodes and the reference electrode, and the like, and regards these principal components as noise to be removed. Thus, the electric reaction measuring apparatus can prevent noise having large influence from remaining in output data without being removed as a result of being regarded as noise having small contribution ratio and small influence due to phase shift.

3. Others

Heretofore, electric reaction measuring apparatuses according to one or more aspects have been described based on embodiments and modifications. However, the present disclosure is not limited to these embodiments and modifications. The scope of one or more aspects may include, within the spirit and scope of the present disclosure, embodiments or modifications modified by a person having ordinary skill in the art and embodiments or modifications constituted by combinations of elements of different embodiments and modifications.

As described above, the technology according to the present disclosure may be implemented in a system, a method, an integrated circuit, a computer program, a computer-readable recording medium such as a compact disc-read only memory (CD-ROM), or any appropriate combination of any of these. Examples of the computer readable recording medium include non-volatile recording media, such as a CD-ROM.

For example, each processor included in the electric reaction measuring apparatus according to the embodiments described above is typically implemented in a large scale integration (LSI), which is an integrated circuit. The processors may be independently integrated into one chip, or some or all of the processors may be integrated into one chip.

The technique for forming an integrated circuit is not limited to LSI and may be implemented by using a dedicated circuit or a general-purpose processor. A field programmable gate array (FPGA), which is programmable after LSI manufacturing, or a reconfigurable processor that allows reconfiguration of connections and settings of circuit cells in an LSI may be used.

In the embodiments described above, each of the constituent elements may be implemented in dedicated hardware or may be implemented by executing a software program suitable for each constituent element. Each constituent element may be implemented in a program execution unit, such as a CPU or a processor, that reads and executes a software program stored in a storage such as a hard disk or a semiconductor memory.

Some or all of the constituent elements described above may be constituted by a removable integrated circuit (IC) card or a single module. The IC card or the module is a computer system composed of a microprocessor, a ROM, a RAM, and the like. The IC card or the module may include the LSI described above or a system LSI. The IC card or the module performs its function as the microprocessor operates in accordance with a computer program. The IC card and the module may be tamper-resistant.

An electric reaction processing method according to an embodiment of the present disclosure may be implemented in a micro processing unit (MPU), a CPU, a processor, a circuit such as an LSI device, an IC card, a stand-alone module, or the like.

The technique disclosed herein may also be implemented in a software program, digital data including a software program, or a non-transitory computer-readable recording medium storing the program. It should be understood that the program can be distributed via a transmission medium such as the Internet.

Numbers, such as ordinal numbers and cardinal numbers, used in the above description are examples for specifically describing the technology according to the present disclosure, and the present disclosure is not limited by the numbers used as examples. The connection relationships between constituent elements are examples for specifically describing the technology according to the present disclosure, and connection relationships for realizing the functions of the present disclosure are not limited to these.

The division of functional blocks in a block diagram is an example, multiple functional blocks may be implemented in one functional block, one functional block may be divided into functional blocks, or some functions may be transferred to another functional block. The functions of functional blocks having similar functions may be processed by single hardware or software parallelly or by time-sharing.

The technology according the present disclosure is widely applicable to apparatuses that measure an electrical reaction of a biological object such as a cell or tissue. For example, the technology according to the present disclosure is useful for observing an electrical reaction of a cell or tissue in an incubator.

What is claimed is:

1. An apparatus comprising:
a culture vessel, wherein the culture vessel includes a partition member disposed on a bottom wall of the culture vessel, wherein the partition member includes one or more chambers, wherein one or more electrodes are disposed in the one or more chambers, wherein each of the one or more electrodes are composed of at least one reference electrode and at least one measurement electrode that are disposed about a partition wall that separates the one or more chambers from each other;
a memory storing a program; and
a processor configured to execute the program to:
measure, for each of the one or more electrodes, a potential of the at least one measurement electrode of the one or more electrodes at one or more predetermined times;
determine at least one principal component for each of the at least one measurement electrode of the one or more electrodes by performing principal component analysis of the potential of each of the at least one measurement electrode of the one or more electrodes at the one or more predetermined times;
estimate, for each of the at least one measurement electrode of the one or more electrodes, a principal component potential due to the principal component from the principal component of the at least one measurement electrode of the one or more electrodes;
synthesize the estimated principal component potential of each of the at least one measurement electrode of the one or more electrodes;
subtract the synthesized estimated principal component potential of each of the at least one measurement electrode of the one or more electrodes from the potential measured at the at least one measurement electrode of the one or more electrodes so as to remove noise; and output a potential difference based on the subtraction that reflects an activity of an object in the culture vessel.

2. The apparatus according to claim 1, further comprising:
a potential meter connected to the at least one measurement electrode of the one or more electrodes and the at least one reference electrode of the one or more electrodes.

3. The apparatus according to claim 1, wherein the partition wall electrically separates the one or more chambers from each other.

4. The apparatus according to claim 3,
wherein the at least one measurement electrode of the one or more electrodes are disposed inside of the partition wall surrounding the one or more chambers, and the at least one reference electrode of the one or more electrodes are disposed on the partition wall.

5. The electric reaction measuring apparatus according to claim 1, wherein the processor is further configured to execute the program to:
determine, for each of the at least one principal component, a contribution ratio of the at least one principal component to a variance of all measured potentials;
extract, from the at least one principal component, a plurality of the at least one principal component in descending order of the contribution ratio; and
synthesize, for each of the plurality of the at least one principal component, potentials corresponding to the plurality of the at least one principal component.

6. The apparatus according to claim 1,
wherein the processor is further configured to execute the program to:
determine at least two principal components for each of the at least one measurement electrode of the one or more electrodes;
determine, regarding the one or more potentials corresponding to the at least two principal components, a correlation coefficient of the one or more potentials corresponding to the at least two of the principal components;
group the two principal components whose correlation coefficient is greater than or equal to a predetermined value into one group;
determine, as a contribution ratio of the one group, a sum of a plurality of contribution ratios of all of the at least one principal component included in the one group;
extract, regarding the contribution ratio of the one group and the plurality of contribution ratios of the at least one principal component that are not included in the one group, the one group and each of the at least one principal component that are not included in the one group in descending order of the contribution ratios;
estimate a sum of potentials corresponding to the at least one principal component that are included in the extracted group and in the extracted at least one principal component that are not included in the group; and
subtract the sum of the potentials from the potential of each of the at least one measurement electrode of the one or more electrodes.

7. A method of an apparatus comprising:
acquiring, for each of one or more electrodes disposed in one or more chambers, a potential of each of at least one measurement electrode of the one or more electrodes at one or more predetermined times, wherein the apparatus comprises a culture vessel that includes a partition member disposed on a bottom wall of the culture vessel, wherein the partition member includes the one or more chambers, wherein each of the one or more electrodes are composed of at least one reference electrode and at least one measurement electrode that are disposed about a partition wall that separates the one or more chambers from each other;
determining at least one principal component for each of the at least one measurement electrode of the one or more electrodes by performing principal component analysis of the potential of each of the at least one measurement electrode of the one or more electrodes at the one or more predetermined times;
estimating, for each of the at least one measurement electrode of the one or more electrodes, a principal component potential corresponding to the principal component from the principal component of the at least one measurement electrode of the one or more electrodes;
synthesizing the estimated principal component potential of each of the at least one measurement electrode of the one or more electrodes;
subtracting the synthesized estimated principal component potential of each of the at least one measurement electrode of the one or more electrodes from the potential acquired for the at least one measurement electrode of the one or more electrodes; and
outputting a potential difference based on the subtraction that reflects an activity of an object in the culture vessel.

8. A non-transitory computer-readable recording medium of an apparatus storing a program that causes a processor to execute a process, the process comprising:
acquiring, for each of one or more electrodes disposed in one or more chambers, a potential of each of at least one measurement electrode of the one or more electrodes at one or more predetermined times, wherein the apparatus comprises a culture vessel that includes a partition member disposed on a bottom wall of the culture vessel, wherein the partition member includes the one or more chambers, wherein one or more electrodes are disposed in the one or more chambers, wherein each of the one or more electrodes are composed of at least one reference electrode and a at least one measurement electrode that are disposed about a partition wall that separates the one or more chambers from each other;
determining at least one principal component for each of the at least one measurement of the one or more electrodes by performing principal component analysis of the potential for each of the at least one measurement of the one or more electrodes at the one or more predetermined times;
estimating, for each of the at least one measurement electrode of the one or more electrodes, a principal component potential corresponding to the principal component from the principal component of the at least one measurement electrode of the one or more electrodes; and
synthesizing the estimated principal component potential of each of the at least one measurement electrode of the one or more electrodes;
subtracting the synthesized estimated principal component potential of each of the at least one measurement electrode of the one or more electrodes from the potential acquired for the at least one measurement electrode of the one or more electrodes so as to remove noise; and outputting a potential difference based on theater subtraction that reflects an activity of an object in the culture vessel.

9. An apparatus comprising:
a culture vessel, wherein the culture vessel includes a partition member disposed on a bottom wall of the culture vessel, wherein the partition member includes one or more chambers, wherein one or more electrodes are disposed in the one or more chambers, wherein each of the one or more electrodes are composed of at least one reference electrode and at least one measurement electrode that are disposed about a partition wall that separates the one or more chambers from each other;
a memory storing a program; and
a processor configured to execute the program to:
(a) acquire a first data series (X11, ..., X1p), ..., an m-th data series (Xm1, ..., Xmp), where
X11 is a first potential at a first measurement electrode of the one or more electrodes at a time t1 with respect to a first reference potential at a reference electrode of the one or more electrodes at the time t1,
X1p is a second potential at the first measurement electrode at a time tp with respect to a second reference potential at the reference electrode at the time tp,
Xm1 is a third potential at an m-th measurement electrode of the one or more electrodes at the time t1 with respect to the third reference potential at the reference electrode at the time t1, and
Xmp is a fourth potential at the m-th electrode at the time tp with respect to the fourth reference potential at the reference electrode at the time tp,
wherein the first measurement electrode is disposed in a first chamber of the one or more chambers in the culture vessel, ..., the m-th measurement electrode is disposed in an m-th chamber of the one or more chambers in the culture vessel, and
wherein a first measurement object is disposed in the first chamber, ..., an m-th measurement object is disposed in the m-th chamber;
(b) obtains a covariance matrix of the first data series (X11, ..., X1p), ..., the m-th data series (Xm1, ..., Xmp);
(c) obtains eigenvalues $\lambda 1, ..., \lambda m$ of the covariance matrix;
(d) obtains, from the eigenvalues $\lambda 1, \lambda 2, ..., \lambda m$, an eigenvector (u1max1 u2max1 ... ummax1) of a largest eigenvalue $\lambda max1$, an eigenvector (u1max2 u2max2 ... ummax2) of a second largest eigenvalue $\lambda max2, ...$ ;
(e) obtains $(\lambda max1/sum) < A$, $\{(\lambda max1 + \lambda max2)/sum\} < A, ..., \{(\lambda max1 + \lambda max2 + ... + \lambda maxi)/sum\} < A$, $\{(\lambda max1 + \lambda max2 + ... + \lambda maxi + \lambda max(i+1))/sum\} > A$, where
A is a predetermined value, and
the sum is $$\sum_{\alpha=1}^{m}(X\alpha 1 - avg1)(X\alpha 1 - avg1)/m + \quad (9)$$

$$... + \sum_{\alpha=1}^{m}(X\alpha m - avgm)(X\alpha m - avgm)/m,$$

where $$avg1 = (X11 + ... + Xm1)/m, ..., avgm = (X1m + ... + Xmm)/m,$$

wherein an eigenvector of $\lambda max1$ is (u1max1 ... ummax1)$^T$, ..., an eigenvalue of $\lambda max(i+1)$ is (u1max(i+1) ... ummax(i+1))$^T$; and
(f) obtains a plurality of potentials by using the eigenvector of $\lambda max1, ...,$ the eigenvector of $\lambda max(i+1)$.

\* \* \* \* \*